US008410066B2

(12) United States Patent
Magnani et al.

(10) Patent No.: US 8,410,066 B2
(45) Date of Patent: Apr. 2, 2013

(54) HETEROBIFUNCTIONAL INHIBITORS OF E-SELECTINS AND CXCR4 CHEMOKINE RECEPTORS

(75) Inventors: John L. Magnani, Gaithersburg, MD (US); Arun K. Sarkar, North Potomac, MD (US)

(73) Assignee: GlycoMimetics, Inc., Gaithersburg, MD (US)

( * ) Notice: Subject to any disclaimer, the term of this patent is extended or adjusted under 35 U.S.C. 154(b) by 301 days.

(21) Appl. No.: 12/768,173

(22) Filed: Apr. 27, 2010

(65) Prior Publication Data

US 2010/0279965 A1 Nov. 4, 2010

Related U.S. Application Data

(60) Provisional application No. 61/174,580, filed on May 1, 2009.

(51) Int. Cl.
*A61K 31/7036* (2006.01)
*C07H 17/02* (2006.01)
*C07H 15/207* (2006.01)
*C07H 3/06* (2006.01)

(52) U.S. Cl. ....... 514/35; 536/17.2; 536/17.9; 536/18.2; 536/4.4

(58) Field of Classification Search .................. None
See application file for complete search history.

(56) References Cited

U.S. PATENT DOCUMENTS

| | | | |
|---|---|---|---|
| 4,471,057 A | 9/1984 | Koprowski et al. | 436/518 |
| 4,851,511 A | 7/1989 | Hakomori et al. | 530/387 |
| 4,859,769 A | 8/1989 | Karlsson et al. | 536/53 |
| 4,876,199 A | 10/1989 | Hakomori | 530/387 |
| 4,925,796 A | 5/1990 | Bergh et al. | 435/97 |
| 4,946,830 A | 8/1990 | Pulverer et al. | 514/23 |
| 5,143,712 A | 9/1992 | Brandley et al. | 424/1.1 |
| 5,151,360 A | 9/1992 | Handa et al. | 435/240.2 |
| 5,211,937 A | 5/1993 | Brandley et al. | 424/1.1 |
| 5,268,364 A | 12/1993 | Kojima et al. | 514/25 |
| 5,304,640 A | 4/1994 | Lasky et al. | 536/23.5 |
| 5,352,670 A | 10/1994 | Venot et al. | 514/54 |
| 5,369,096 A | 11/1994 | Yamada et al. | 514/61 |
| 5,412,123 A | 5/1995 | Rao et al. | 552/290 |
| 5,444,050 A | 8/1995 | Kogan et al. | 514/25 |
| 5,464,778 A | 11/1995 | Cummings et al. | 436/503 |
| 5,464,815 A | 11/1995 | Chamow et al. | 514/8 |
| 5,470,843 A | 11/1995 | Stahl et al. | 514/61 |
| 5,484,891 A | 1/1996 | Lasky et al. | 530/387.3 |
| 5,486,536 A | 1/1996 | Ward et al. | 514/460 |
| 5,519,008 A | 5/1996 | Rao et al. | 514/26 |
| 5,527,785 A | 6/1996 | Bevilacqua et al. | 514/56 |
| 5,538,724 A | 7/1996 | Butcher et al. | 424/152.1 |
| 5,559,103 A | 9/1996 | Gaeta et al. | 514/54 |
| 5,576,305 A | 11/1996 | Ratcliffe | 514/25 |
| 5,580,858 A | 12/1996 | Ippolito et al. | 514/25 |
| 5,580,862 A | 12/1996 | Rosen et al. | 514/61 |
| 5,589,465 A | 12/1996 | Ishida et al. | 514/25 |
| 5,604,207 A | 2/1997 | DeFrees et al. | 514/25 |
| 5,618,785 A | 4/1997 | Heavner et al. | 514/2 |
| 5,622,937 A | 4/1997 | Kogan et al. | 514/25 |
| 5,632,991 A * | 5/1997 | Gimbrone, Jr. | 424/178.1 |
| 5,639,734 A | 6/1997 | Esko et al. | 514/25 |
| 5,646,123 A | 7/1997 | Ippolito et al. | 514/25 |
| 5,646,248 A | 7/1997 | Sawada et al. | 530/350 |
| 5,648,344 A | 7/1997 | Brandley et al. | 514/61 |
| 5,654,282 A | 8/1997 | Tang et al. | 514/25 |
| 5,654,412 A | 8/1997 | Srivastava et al. | 536/18.5 |
| 5,658,880 A | 8/1997 | Dasgupta et al. | 514/8 |
| 5,663,151 A | 9/1997 | Martel et al. | 514/25 |
| 5,679,321 A | 10/1997 | Dasgupta et al. | 424/9.1 |
| 5,679,644 A | 10/1997 | Rao et al. | 514/26 |
| 5,686,426 A | 11/1997 | Martel et al. | 514/25 |
| 5,693,621 A | 12/1997 | Toepfer et al. | 514/25 |
| 5,695,752 A | 12/1997 | Rosen et al. | 424/94.61 |
| 5,710,023 A | 1/1998 | Collins et al. | 435/69.1 |
| 5,710,123 A | 1/1998 | Heavner et al. | 514/2 |
| 5,723,583 A | 3/1998 | Seed et al. | 530/387.3 |
| 5,728,685 A | 3/1998 | Abbas et al. | 514/53 |
| 5,739,300 A | 4/1998 | Toepfer et al. | 536/4.1 |
| 5,747,463 A | 5/1998 | Marinier et al. | 514/25 |
| 5,750,508 A | 5/1998 | Dasgupta et al. | 514/25 |
| 5,753,617 A | 5/1998 | Heavner et al. | 514/9 |
| 5,753,631 A | 5/1998 | Paulson et al. | 514/25 |

(Continued)

FOREIGN PATENT DOCUMENTS

DE 2434953 2/1975
EP 319253 A2 6/1989

(Continued)

OTHER PUBLICATIONS

Zhang et al., "Chemokine CXCL12 and its receptor CXCR4 expression are associated with perineural invasion of prostate cancer" Journal of Experimental and Clinical Cancer Research (2008) vol. 27 No. 61, pp. 1-9.*
Oxford Textbook of Oncology, vol. 1, published 1995 by Oxford University Press, pp. 447-453.*
The Merck Manual of Diagnosis and Therapy, Seventeenth Edition, published 1999 by Merck Research Laboratories, pp. 397, 398, 948,949, 1916, 1979-1981.*
Zesig et al., "Effect of sialyl Lewis X-glycoliposomes on the inhibition of E-selectin-mediated tumour cell adhesion in vitro" Biochimica et Biophysica Acta (2004) 1660, pp. 31-40.*
Abraham, W.M. et al., "Selectin Blockade Prevents Antigen-induced Late Bronchial Response and Airway Hyperresponsiveness in Allergic Sheep," *Am J. Respir Crit Care Med. 159*: 1205-1214, 1999.
Acord, J. et al., "A rapid microplate method for quantifying inhibition of bacterial adhesion to eukaryotic cells," *Journal of Microbiological Methods 60*: 55-62, 2005.
Arakaki, R. et al., "T134, a Small-Molecule CXCR4 Inhibitor, Has No Cross-Drug Resistance with AMD3100, a CXCR4 Antagonist with a Different Structure," *Journal of Virology* 73(2):1719-1723, Feb. 1999.

(Continued)

*Primary Examiner* — Eric S Olson

(74) *Attorney, Agent, or Firm* — Seed IP Law Group PLLC

(57) ABSTRACT

Compounds, compositions and methods are provided for treating cancer and inflammatory diseases, and for releasing cells such as stem cells (e.g., bone marrow progenitor cells) into circulating blood and enhancing retention of the cells in the blood. More specifically, heterobifunctional compounds that inhibit both E-selectins and CXCR4 chemokine receptors are described.

33 Claims, 8 Drawing Sheets

U.S. PATENT DOCUMENTS

| | | | | |
|---|---|---|---|---|
| 5,763,413 | A | 6/1998 | Numata et al. | 514/25 |
| 5,763,582 | A | 6/1998 | Rao et al. | 536/5 |
| 5,789,385 | A | 8/1998 | Anderson et al. | 514/25 |
| 5,789,573 | A | 8/1998 | Baker et al. | 536/24.5 |
| 5,795,958 | A | 8/1998 | Rao et al. | 530/331 |
| 5,811,404 | A | 9/1998 | De Frees et al. | 514/25 |
| 5,811,405 | A | 9/1998 | Toepfer et al. | 514/25 |
| 5,817,742 | A | 10/1998 | Toepfer et al. | 528/328 |
| 5,827,817 | A | 10/1998 | Larsen et al. | 514/2 |
| 5,827,837 | A | 10/1998 | Bevilacqua et al. | 514/103 |
| 5,830,871 | A | 11/1998 | Wong et al. | 514/23 |
| 5,837,689 | A | 11/1998 | Anderson et al. | 514/25 |
| 5,837,690 | A | 11/1998 | Rao et al. | 514/26 |
| 5,840,679 | A | 11/1998 | Larsen et al. | 514/8 |
| 5,854,218 | A | 12/1998 | DeFrees | 514/25 |
| 5,858,983 | A | 1/1999 | Seed et al. | 514/23 |
| 5,858,994 | A | 1/1999 | Kretzschmar et al. | 514/62 |
| 5,880,091 | A | 3/1999 | Cummings et al. | 514/8 |
| 5,916,910 | A | 6/1999 | Lai | 514/423 |
| 5,919,768 | A | 7/1999 | Korgan et al. | 514/25 |
| 5,919,769 | A | 7/1999 | Tsukida et al. | 514/25 |
| 5,962,422 | A | 10/1999 | Nagy et al. | 514/25 |
| 5,976,540 | A | 11/1999 | Rittershaus et al. | 424/184.1 |
| 5,977,080 | A | 11/1999 | Rosen et al. | 514/25 |
| 5,985,852 | A | 11/1999 | Nagy et al. | 514/54 |
| 5,994,402 | A | 11/1999 | Rotstein et al. | 514/547 |
| 6,001,819 | A | 12/1999 | Simon et al. | 514/54 |
| 6,001,988 | A | 12/1999 | Parma et al. | 536/24.3 |
| 6,033,665 | A | 3/2000 | Yednock et al. | 424/130.1 |
| 6,037,333 | A | 3/2000 | Panjwani | 514/62 |
| 6,110,897 | A | 8/2000 | Unverzagt et al. | 514/25 |
| 6,111,065 | A | 8/2000 | Heavner et al. | 530/300 |
| 6,120,751 | A | 9/2000 | Unger | 424/9.51 |
| 6,121,233 | A | 9/2000 | Magnani et al. | 514/8 |
| 6,124,267 | A | 9/2000 | McEver et al. | 514/25 |
| 6,133,239 | A | 10/2000 | Handa et al. | 514/25 |
| 6,133,240 | A | 10/2000 | Taylor et al. | 514/25 |
| 6,136,790 | A | 10/2000 | Toepfer et al. | 514/25 |
| 6,169,077 | B1 | 1/2001 | Oehrlein | 514/25 |
| 6,177,547 | B1 | 1/2001 | Cummings et al. | 530/388.22 |
| 6,187,754 | B1 | 2/2001 | Oehrlein | 514/25 |
| 6,193,973 | B1 | 2/2001 | Tuttle | 424/195.1 |
| 6,193,979 | B1 | 2/2001 | Rittershaus et al. | 424/195.11 |
| 6,197,752 | B1 | 3/2001 | Schmidt et al. | 514/23 |
| 6,225,071 | B1 | 5/2001 | Cummings et al. | 435/7.24 |
| 6,235,309 | B1 | 5/2001 | Nagy et al. | 424/450 |
| 6,280,932 | B1 | 8/2001 | Parma et al. | 435/6 |
| 6,309,639 | B1 | 10/2001 | Cummings et al. | 424/143.1 |
| 6,387,884 | B1 | 5/2002 | Magnani et al. | 514/25 |
| 6,391,857 | B1 | 5/2002 | Magnani et al. | 514/25 |
| 6,407,135 | B1 | 6/2002 | Lai et al. | 514/423 |
| 6,465,434 | B1 | 10/2002 | Magnani et al. | 514/25 |
| 6,492,332 | B1 | 12/2002 | Demopulos et al. | 514/12 |
| 6,503,885 | B1 | 1/2003 | Kiso et al. | 514/25 |
| 6,528,487 | B1 | 3/2003 | Heavner et al. | 514/13 |
| 7,060,685 | B2 | 6/2006 | Magnani et al. | 514/25 |
| 7,422,733 | B2 | 9/2008 | Ranganathan et al. | |
| 7,728,117 | B2 | 6/2010 | Magnani et al. | 536/16.7 |
| 2001/0046970 | A1 | 11/2001 | Nagy et al. | 514/53 |
| 2001/0051370 | A1 | 12/2001 | Bistrup et al. | 435/193 |
| 2002/0026033 | A1 | 2/2002 | Cummings et al. | 530/322 |
| 2002/0028205 | A1 | 3/2002 | Holgersson et al. | 424/184.1 |
| 2002/0031508 | A1 | 3/2002 | Wagner et al. | 424/94.63 |
| 2002/0040008 | A1 | 4/2002 | Wagner et al. | 514/41 |
| 2002/0132220 | A1 | 9/2002 | Berens et al. | 435/1.1 |
| 2002/0164336 | A1 | 11/2002 | Harrison et al. | 424/146.1 |
| 2002/0164748 | A1 | 11/2002 | Bistrup et al. | 435/193 |
| 2002/0168366 | A1 | 11/2002 | Stewart et al. | 424/146.1 |
| 2003/0012787 | A1 | 1/2003 | Ashkenazi et al. | 424/145.1 |
| 2003/0012790 | A1 | 1/2003 | Ashkenazi et al. | 424/178.1 |
| 2003/0018181 | A1 | 1/2003 | Larsen et al. | 536/23.4 |
| 2003/0039683 | A1 | 2/2003 | Cantrell et al. | 424/450 |
| 2004/0096396 | A1 | 5/2004 | Magnani et al. | |
| 2005/0187171 | A1 | 8/2005 | Magnani et al. | 514/43 |
| 2006/0264451 | A1 | 11/2006 | Shim et al. | 514/275 |
| 2007/0054930 | A1 | 3/2007 | Shim et al. | 514/275 |
| 2008/0161546 | A1 | 7/2008 | Ernst et al. | 536/17.9 |
| 2008/0227799 | A1 | 9/2008 | Liotta et al. | 514/275 |
| 2009/0312278 | A1* | 12/2009 | Magnani et al. | 514/35 |

FOREIGN PATENT DOCUMENTS

| | | |
|---|---|---|
| EP | 381310 A1 | 8/1990 |
| EP | 408859 B1 | 8/1995 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01335 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 99/42130 | 8/1999 |
| WO | WO 99/43353 | 9/1999 |
| WO | WO 99/43356 | 9/1999 |
| WO | WO 00/02870 | 1/2000 |
| WO | WO 02/22820 | 3/2002 |
| WO | WO 02/062810 | 8/2002 |
| WO | WO 03/055876 | 7/2003 |
| WO | WO 03/097658 | 11/2003 |
| WO | WO 2004/004636 | 1/2004 |
| WO | WO 2004/058304 | 7/2004 |
| WO | WO 2005/054264 | 6/2005 |
| WO | WO 2005/116088 | 12/2005 |
| WO | WO 2006/074426 | 7/2006 |
| WO | WO 2006/074428 | 7/2006 |
| WO | WO 2006/127906 | 11/2006 |
| WO | WO 2007/028050 | 3/2007 |
| WO | WO 2008/008852 | 1/2008 |
| WO | WO 2008/008854 | 1/2008 |
| WO | WO 2008/060378 | 5/2008 |
| WO | WO 2009/152245 | 11/2009 |
| WO | WO 2010/126888 | 11/2010 |

OTHER PUBLICATIONS

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem.* 266(32):21537-21547, 1991.

Bänteli, R. et al., "Potent E-Selectin Antagonists," Helvetica Chimica Acta 83(11): 2893-2907, 2000.

Belcher, J.D. et al., "Activated monocytes in sickle cell disease: potential role in the activation of vascular endothelium and vaso-occlusion," Blood, 96(7): 2451-2459, Oct. 1, 2000.

Belcher, J.D. et al., "Inflammatory Response in Transgenic Mouse Models of Human Sickle Cell Anemia," Abstract #2574, Blood, 96(11): 600a, Nov. 16, 2000.

Berg et al., "A Carbohydrate Domain Common to Both Sialyl Lea and Sialyl Lex Is Recognized by the Endothelial Cell Leukocyte Adhesion Molecule ELAM-1," J. Biol. Chem. 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.

Bird and Kimber, "Oligosaccharides Containing Fucose Linked α(1-3) and α(1-4) to N-Acetylglucosamine Cause Decompaction of Mouse Morulae," Devel. Biol. 104:449-460, 1984.

Blanc-Muesser, et al., "Syntheses Stereoselective de 1-Thioglycosides," Carbohydrate Research 67:305-328, 1978.

Bock, K. et al., "Conformations in Solution of α,α-Trehalose, α-D-Glucopyranosyl α-D-Mannopyranoside, and Their 1-Thioglycosyl Analogs, and a Tentative Correlation of Their Behaviour with Respect to the Enzyme Trehalase," European Journal of Biochemistry 131:595-600, 1983.

Bowen et al., "Characterization of a Human Homologue of the Murine Peripheral Lymph Node Homing Receptor," Journal of Cell Biology 109:421-427, 1989.

Brandley et al., "Carbohydrate Ligands of LEC Cell Adhesion Molecules," Cell 63:861-863, 1990.

Broquet et al., "Effect of Desipramine on a Glycoprotein Sialyltransferase Activity in C6 Cultured Glioma Cells," J. Neurochem. 54:388-394, 1990.

Cao, X. et al., "Defective Lymphoid Development in Mice Lacking Expression of the Common Cytokine Receptor γ Chain," *Immunity* 2:223-238, Mar. 1995.

Ceder, O. et al., "On the Absolute Configuration of 3-Cyclohexene-1-carboxylic Acid," Acta Chemica Scandinavica 24(8):2693-2698, 1970.

Chemical Abstracts (STN), Accession No. 1997:5843307, Jul. 8, 1997.

Childs et al., "High-molecular-weight glycoproteins are the major carriers of the carbohydrate differentiation antigens I, i and SSEA-1 of mouse teratocarcinoma cells," Biochem. J. 215:491-503, 1983.

Christianson, S.W. et al., "Enhanced Human $CD^+$ T Cell Engraftment in $\beta_2$-Microglobulin-Dificient NOD-*scid* Mice," *The Journal of Immunology* 158:3578-3586, 1997.

Cleophax, J. et al., "A Chiral Synthesis of D-(+)-2,6-Dideoxystreptamine and Its Microbial Incorporation into Novel Antibiotics," Journal of the American Chemical Society, 98(22): 7110-7112, Oct. 27, 1976.

Corral et al., "Requirements for Sialic Acid on Neutrophils in a GMP-140 (PADGEM) Mediated Adhesive Interaction with Activated Platelets," Biochem. Biophys. Res. Commun. 172:1349-1356, 1990.

Datta and Takayama, "Isolation and purification of trehalose 6-mono- and 6,6'-dicorynomycolates from *Cornyebacterium matruchotii*. Structural characterization of 1H NMR," Carbohydrate Research 245: 151-158, 1993.

Doranz, B.J. et al., "Safe Use of the CSCR4 Inhibitor ALX40-4C in Humans," *AIDS Research and Human Retroviruses* 17(6):475-486, 2001.

Duijvestijn et al., "High Endothelial Differentiation in Human Lymphoid and Inflammatory Tissues Defined by Monoclonal Antibody HECA-452," Am. J. Path. 130:147-155, 1988.

Dupré, B. et al., "Glycomimetic Selectin Inhibitors: (α-D-Mannopyranosyloxy)methylbiphenyls," Bioorganic & Medicinal Chemistry Letters 6(5): 569-572, 1996.

Edgington, "How Sweet It Is: Selectin-Mediating Drugs," Biotechnology 10: 383-389, 1992.

Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.

Eggens et al., "Specific Interaction between Lex and Lex Determinants. A Possible Basis for Cell Recognition in Preimplantation Embryos and in Embryonal Carcinoma Cells," J. Biol. Chem. 264(16):9476-9484, 1989.

Embury, S.H. et al., "The contribution of endothelial cell P-selectin to the microvascular flow of mouse sickle erythrocytes in vivo," Blood, 104(10): 3378-3385, Nov. 15, 2004.

Ernst and Oehrlein, "Substrate and donor specificity of glycosyl transferases," Glycoconjugate Journal 16: 161-170, 1999.

Ernst, B. et al., "Design and Synthesis of E-Selectin Antagonists," *Chimia* 55(4):268-274, 2001.

Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.

Fenderson et al., "Coordinate Expression of X and Y Haptens during Murine Embryogenesis," Devel. Biol. 114:12-21, 1986.

Fenderson et al., "The blood group I antigen defined by monoclonal antibody C6 is a marker of early mesoderm during murine embryogenesis," Differentiation 38:124-133, 1988.

Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.

Fukushi et al., "Novel Fucolipids Accumulating in Human Adenocarcinoma. III. A Hybridoma Antibody (FH6) Defining a Human Cancer-Associated Difucoganglioside (VI3NeuAcV3III3Fuc2nLc6)," J. Biol. Chem. 259(16):10511-10517, 1984.

Gabius et al., "Endogenous Tumor Lectins: Overview and Perspectives," Anticancer Res. 6:573-578, 1986.

Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.

Gallatin et al., "A cell-surface molecule involved in organ-specific homing of lymphocytes," Nature 304:30-34, 1983.

Gooi et al., "Stage-specific embryonic antigen involves α 1 → 3 fucosylated type 2 blood group chains," Nature 292:156-158, 1981.

Hakomori et al., "Novel Fucolipids Accumulating in Human Adenocarcinoma. I. Glycolipids With Di- or Trifucosylated Type 2 Chain," J. Biol. Chem. 259(7):4672-4680, 1984.

Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.

Hakomori S., "Aberrant Glycosylation in Cancer Cell Membranes as Focused on Glycolipids: Overview and Perspectives," Cancer Res. 45:2405-2414, 1985.

Handa et al., "Selectin GMP-140 (CD62; PADGEM) Binds to Sialosyl-Lea and Sialosyl-Lex, and Sulfated Glycans Modulate this Binding," Biochemical and Biophysical Research Communication 181(3):1223-1230, 1991.

Hansson and Zopf, "Biosynthesis of the Cancer-associated Sialyl-Lea Antigen," Journal of Biological Chemistry 260(16):9388-9392, 1985.

Harlan, John M., "Introduction: anti-adhesion therapy in sickle cell disease," Blood, 95(2): 365-367, Jan. 15, 2000.

Hasegawa et al., "Synthesis of deoxy-L-fucose-containing sialyl Lewis X ganglioside analogues," Carbohydrate Research 257: 67-80, 1994.

Hasegawa et al., "Synthesis of sialyl Lewis X ganglioside analogues containing modified L-fucose residues," Carbohydrate Research 274: 165-181, 1995.

Hebbel, R.P., "Blockade of Adhesion of Sickle Cells to Endothelium by Monoclonal Antibodies," The New England Journal of Medicine, 342(25): 1910-1912, Jun. 22, 2000.

Hendrix, C.W. et al., "Pharmacokinetics and Safety of AMD-3100, a Novel Antagonist of the CXCR-4 Chemokine Receptor, in Human Volunteers," *Antimicrobial Agents and Chemotherapy* 44(6):1667-1673, Jun. 2000.

Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

Huse et al., "Generation of a Large Combinatorial Library of the Immunoglobulin Repertoire in Phage Lambda," Science 246:1275-1281, 1989.

Huwe, C.M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.

Hynes, R., "Integrins: A Family of Cell Surface Receptors," Cell 48:549-554, 1987.

Inwald, D.P. et al., "Platelet and leucocyte activation in childhood sickle cell disease: association with nocturnal hypoxaemia," British Journal of Haematology, 111(2): 474-481, Nov. 2000.

Ishikawa, F. et al., "Chemotherapy-resistant human AML stem cells home to and engraft within the bone-marrow endosteal region," *Nature Biotechnology* 25(11):1315-1321, Nov. 2007.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.

Itai, S. et al., "Differentiation-dependent Expression of I and Sialyl I Antigens in the Developing Lung of Human Embryos and in Lung Cancers," Cancer Research 50: 7603-7611, 1990.

Jeffrey et al., "Affinity Chromatography of Carbohydrate-Specific Immunoglobulins: Coupling of Oligosaccharides to Sepharose," Biochem. Biophys. Res. Commun. 62:608-613, 1975.

Jentsch, K.D. et al., "Inhibition of Human Immunodeficiency Virus Type I Reverse Transcriptase by Suramin-related Compounds," The Journal of General Virology 68(8): 2183-2192, 1987.

Kaila, N. et al., "Design and Synthesis of Sialyl Lewis Mimics as E- and P-Selectin Inhibitors," Medicinal Research Reviews, 22(6):566-601, 2002.

Kaila, N. et al., "β-C-Mannosides as Selectin Inhibtors," Journal of Medicinal Chemistry 45(8):1563-1566, 2002.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.

Kannagi et al., "Stage-specific embryonic antigens (SSEA-3 and -4) are epitopes of a unique globo-series ganglioside isolated from human teratocarcinoma cells," Embo J. 2(12):2355-2361, 1983.

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.

Kaul, D.K. et al., "Hypoxia/reoxygenation causes inflammatory response in transgenic sickle mice but not in normal mice," The Journal of Clinical Investigation, 106(3): 411-420, Aug. 2000.

Kitagawa et al., "Characterization of Mucin-Type Oligosaccharides With the Sialyl-Lea Structure From Human Colorectal Adenocarcinoma Cells," Biochem. Biophys. Res. Commun. 178(3):1429-1436, 1991.

Kitagawa et al., "Immunoaffinity Isolation of a Sialyl-Lea Oligosaccharide from Human Milk," J. Biochem. 104:591-594, 1988.

Kneuer, C. et al., "Selectins—potential pharmacological targets?" Drug Discovery Today, 11(21/22): 1034-1040, Nov. 2006.

Kogan, T.P et al., "Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.

Kogan, T.P. et al., "Novel Synthetic Inhibitors of Selectin-Mediated Cell Adhesion: Synthesis of 1,6-Bis[3-(3-carboxymethylphenyl)-r-(2-α-D-monnopyranosyloxy)phenyl]hexane (TBC1269)," J. Med. Chem 41:1099-1111, 1998.

Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," J. Med. Chem. 38: 4976-4984, Dec. 22, 1995.

Köhler and Milstein, "Continuous cultures of fused cells secreting antibody of predefined specificity," Nature 256:495-497, 1975.

Köhler and Milstein, "Derivation of specific antibody-producing tissue culture and tumor lines by cell fusion," Eur. J. Immunol. 6:511-519, 1976.

Kojima and Hakomori, "Specific Interaction between Gangliotriaosylceramide (Gg3) and Sialosyllactosylceramide (GM3) as a Basis for Specific Cellular Recognition between Lymphoma and Melanoma Cells," J. Biol. Chem. 264(34):20159-20162, 1989.

Kolb, H.C. et al., "Development of Tools for the Design of Selectin Antagonists," Chem. Eur. J. 3(10):1571-1578, 1997.

Kolb, H.C. et al., "Recent progress in the glycodrug area," Pure & Applied Chemistry 69(9):1879-1884, 1997.

Koprowski et al., "Colorectal Carcinoma Antigens Detected by Hybridoma Antibodies," Somatic Cell Genetics 5(6):957-972, 1979.

Kuzuoka, "Antitumor activity of murine monoclonal antibody NCC-ST-421," Chem. Ab. 115:27344v, 1991.

Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→•) Structural Element Revealed by 500-Mhz H NMR Spectroscopy," Journal of Biological Chemistry 259(14):9051-9058, 1984.

Larsen et al., PADGEM-Dependent Adhesion of Platelets to Monocytes and Neutrophils Is Mediated by a Lineage-Specific Carbohydrate, LNF III (CD15), Cell 63:467-474, 1990.

Lindenberg et al., "Carbohydrate binding properties of mouse embryos," J. Reprod. Fert. 89:431-439, 1990.

Lipartiti et al., "Monosialoganglioside GM1 Reduces NMDA Neurotoxicity in Neonatal Rat Brain," Experimental Neurology 113:301-305, 1991.

Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.

Lowe et al., "ELAM-1-Dependent Cell Adhesion to Vascular Endothelium Determined by a Transfected Human Fucosyltransferase cDNA," Cell 63:475-484, 1990.

Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.

Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.

Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.

Magnani, J., "Carbohydrate Sequences Detected by Murine Monoclonal Antibodies," Chemistry and Physics of Lipids 42:65-74, 1986.

Magnani, J., "Potent Glycomimetic Inhibitors of the Adhesion Molecule, PA-IIL, for the Bacterial Pathogen, *Pseudomonas auroginosa*," Glycobiology 13(11): 854, Abstract No. 104, Oct. 2003.

Matsui, N.M. et al., "Heparin inhibits the flow adhesion of sickle red blood cells to P-selectin," Blood, 100(10): 3790-3796, Nov. 15, 2002.

Matsui, N.M. et al., "P-selectin mediates the adhesion of sickle erythrocytes to the endothelium," Blood, 98(6): 1955-1962, Sep. 15, 2001.

Matsui, N.M. et al., "The Novel Adhesion of Erythrocytes to P-Selectin in Sickle Cell Disease," Abstract #2575, Blood, 96(11): 600a, Nov. 16, 2000.

Mulligan and Berg, "Selection for animal cells that express the *Escherichia coli* gene coding for xanthine-gunine phosphoribosyltransferase," Proc. Natl. Acad. Sci. USA 78:2072-2076, 1981.

Nagel, R.L., "A Knockout of a Transgenic Mouse—Animal Models of Sickle Cell Anemia," The New England Journal of Medicine, 339(3):194-195, Jul. 16, 1998.

Natarajan, M. et al., "Adhesion of Sickle Red Blood Cells and Damage to Interleukin-1β Stimulated Endothelial Cells Under Flow in Vitro," Blood, 87(11): 4845-4852, Jun. 1, 1996.

Nicolaou et al., "Total Synthesis of the Tumor-Associated Lex Family of Glycosphingolipids," J. Amer. Chem. Soc. 112:3693-3695, 1990.

Nudelman et al., "Novel Fucolipids of Human Adenocarcinoma: Disialosyl Lea Antigen (III4FucIII6NeuAcIV3NeuAcLc4) of Human Colonic Adenocarcinoma and the Monoclonal Antibody (FH7) Defining This Structure," J. Biol. Chem. 261:5487-5495, 1986.

Örhlein, R., "Carbohydrates and Derivatives as Potential Drug Candidates with Emphasis on the Selectin and Linear-B Area," Mini Reviews in Medicinal Chemistry 1: 349-361, 2001.

Palcic et al., "Enzymic Synthesis of Oligosaccharides Terminating in the Tumor-Associated Sialyl-Lewis-a Determinant," Carbohydr. Res. 190:1-11, 1989.

Palcic et al., "Regulation of N-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," J. Biol. Chem. 265:6759-6769, 1990.

Palcic et al., "A Bisubstrate Analog Inhibitor for α(1→2)-Fucosyltransferase," J. Biol. Chem. 264:17174-17181, 1989.

Palma-Vargas, J.M. et al., "Small-Molecule Selectin Inhibitor Protects Against Liver Inflammatory Response After Ischemia and Reperfusion," J. Am. Coll. Surg. 185: 365-372, 1997.

Patton, J.T. et al., "GMI-1070: a Small, Glycomimetic, Pan-selectin Antagonist that Improves Blood Flow and Inhibits Blood Cell Adhesion in Sickle Mice," Glyco XIX, Gaithersburg, Maryland, Sep. 2, 2005. Available from http://ww.glycomimetics.com/library. Accessed Jun. 10, 2009.

Perret, S. et al., "Structural basis for the interaction between human milk oligosaccharides and the bacterial lectin PA-ILL of *Pseudomonas aeruginosa*," Biochem. J. 389: 325-332, 2005.

Phillips et al., "ELAM-1 Mediates Cell Adhesion by Recognition of a Carbohydrate Ligand, Sialyl-Lex," Science 250:1130-1132, 1990.

Picker et al., "The Neutrophil Selectin LECAM-1 Presents Carbohydrate Ligands to the Vascular Selectins ELAM-1 and GMP-140," Cell 66:921-933, 1991.

Prokazova et al., "Sialylated lactosylceramides. Possible inducers of non-specific immunosuppression and atherosclerotic lesions," European Journal of Biochemistry 172:1-6, 1988.

Purton, L. E. et al., "Limiting Factors in Murine Hematopoietic Stem Cell Assays," *Cell Stem Cell 1*: 263-270, Sep. 2007.

Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.

Rice and Bevilacqua, "An Inducible Endothelial Cell Surface Glycoprotein Mediates Melanoma Adhesion," Science 246:1303-1306, 1989.

Ruoslahti and Pierschbacher, "New Perspectives in Cell Adhesion: RGD and Integrins," Science 238:491-497, 1987.

Sakurai et al., "Selection of a Monoclonal Antibody Reactive with a High-MolecularWeight Glycoprotein Circulating in the Body Fluid of Gastrointestinal Cancer Patients," Cancer Research 48:4053-4058, 1988.

Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.

Scharfman, A. et al., "*Pseudomonas aeruginosa* binds to neoglycoconjugates bearing mucin carbohydrate determinants and predominantly to sialyl-Lewis x conjugates," Glycobiology 9(8): 757-764, 1999.

Scharfman, A. et al., "Recognition of Lewis x Derivatives Present on Mucins by Flagellar Components of *Pseudomonas aeruginosa*," Infection and Immunity 69(9): 5243-5248, Sep. 2001.

Shitara et al., "Application of Anti-Sialyl Lea Monoclonal antibody, KM231, for Immunotherapy of Cancer," Anticancer Res. 11:2003-2014, 1991.

Siuzdak et al., "Examination of the Sialyl Lewis X—Calcium Complex by Electrospray Mass Spectrometry," Bioorganic & Medicinal Chemistry Letters 4(24): 2863-2866, 1994.

Solovey, A. et al., "Circulating Activated Endothelial Cells in Sickle Cell Anemia," The New England Journal of Medicine, 337(22): 1584-1590, Nov. 27, 1997.

Solovey, AA., et al., "Modulation of endothelial cell activation in sickle cell disease: a pilot study," Blood, 97(7): 1937-1941, Apr. 1, 2001.

Sprengard, U. et al., "Synthesis and Biological Activity of Novel Sialyl-LewisX Conjugates," Bioorganic & Medicinal Chemistry Letters 6(5): 509-514, 1996.

Stanley and Atkinson, "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.

Stephens and Cockett, "The construction of highly efficient and versatile set of mammalian expression vectors," Nucleic Acids Research. 17:7110, 1989.

Streeter et al., "Immunohistologic and Functional Characterization of a Vascular Addressin Involved in Lymphocyte Homing into Peripheral Lymph Nodes," Journal of Cell Biology 107: 1853-1862, 1988.

Stroud et al., "Extended Type 1 Chain Glycosphingolipids: Dimeric Lea (III4V4Fuc2Lc6) as Human Tumor-associated Antigen," J. Biol. Chem. 266(13):8439-8446, 1991.

Svenson and Lindberg, "Coupling of Acid Labile Salmonella Specific Oligosaccharides to Macromolecular Carriers," J. Immunol. Meth. 25:323-335, 1979.

Takada et al., "Adhesion of Human Cancer Cells to Vascular Endothelium Mediated by a Carbohydrate Antigen, Sialyl Lewis A1," Biochem. Biophys. Res. Commun. 179(2):713-719, 1991.

Takeichi, M., "Cadherins: a molecular family essential for selective cell-cell adhesion and animal morphogenesis," Trends Genet. 3(8):213-217, 1987.

Thoma, G. et al., "A readily Available, Highly Potent E-Selectin Antagonist," Angew. Chem. Int. Ed. 40(19): 3644-3647, 2001.

Thoma, G. et al., "Preorganization of the Bioactive Conformation of Sialyl LewisX Analogues Correlates with Their Affinity to E-Selectin," Angew. Chem. Int. Ed. 40(10): 1941-1945, 2001.

Thoma, G. et al., "Synthesis and Biological Evaluation of a Potent E-Selectin Antagonist," J. Med. Chem., 42: 4909-4913, 1999.

Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.

Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.

Turhan, A. et al., "Primary role for adherent leukocytes in sickle cell vascular occlusion: A new paradigm," Proceedings of the National Academy of Sciences, 99(5): 3047-3051, Mar. 5, 2002.

Tyrrell et al., "Structural requirements for the carbohydrate ligand of E-selectin," Proc. Natl. Acad. Sci. USA 88:10372-10376, 1991.

Waldmann, H. et al., "Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.

Walz et al., "Recognition by ELAM-1 of the Sialyl-Lex Determinant on Myeloid and Tumor Cells," Science 250:1132-1135, 1990.

Ward and Mulligan, "Blocking of adhesion molecules in vivo as anti-inflammatory therapy," Immunology 1: 165-171, 1994.

Whisler and Yates, "Regulation of Lymphocyte Responses by Human Gangliosides. I. Characteristics of Inhibitory Effects and the Induction of Impaired Activation," Journal of Immunology 125(5):2106-2111, 1980.

Yamazaki, F. et al., "Syntheisis of an appropriately protected core glycotetraoside, a key intermediate for the synthesis of 'bisected' complex-type glycans of a glycoprotein," Carbohydrate Research 201: 15-30, 1990.

Zhou et al., "The Selectin GMP-140 Binds to Sialylated, Fucosylated Lactosaminoglycans on Both Myeloid and Nonmyeloid Cells," Journal of Cell Biology 115(2):557-564, 1991.

Zopf et al., "Affinity Purification of Antibodies Using Oligosaccharide-Phenethylamine Derivatives Coupled to Sepharose," Meth. Enzymol. 50:171-175, 1978.

Crawford et al., "AMD070, a CXCR4 Chemokine Receptor Antagonist: Practical Large-Scale Laboratory Synthesis," *Org. Process Res. Devel. 12*:823-830, 2008.

De Clercq, Erik, "The bicyclam AMD3100 story," *Nat. Rev. Drug Disc. 2*:581-587, Jul. 2003.

Faber et al., "The Many Facets of SDF-1α, CXCR4 Agonists and Antagonists on Hematopoietic Progenitor Cells," *J. Biomed. & Biotech.* Article ID 26065:1-10, 2007.

Kim et al., "Inhibition of the CXCR4/CXCL12 Chemokine Pathway Reduces the Development of Murine Pulmonary Metastases," *Clin. Exp. Metastasis* 25(3):201-211, 2008.

Kwong et al., "An Antagonist of the Chemokine Receptor CXCR4 Induces Mitotic Catastrophe in Ovarian Cancer Cells," *Mol. Cancer Ther.* 8(7): 1893-1905, Jul. 2009.

Loetscher et al., "N-terminal Peptides of Stromal Cell-derived Factor-1 with CXC Chemokine Receptor 4 Agonist and Antagonist Activities," *J. Biol. Chem.* 273(35):22279-22283, 1998.

Mosley et al., "Recent Patents Regarding the Discovery of Small Molecule CXCR4 Antagonists," *Expert Opin. Ther. Patents* 19(1):23-38, 2009.

Richert et al., "Inhibition of CXCR4 by CTCE-9908 Inhibits Breast Cancer Metastasis to Lung and Bone," *Oncology Reports* 21:761-767, 2009.

Singh et al., "Evaluation of a CXCR4 Antagonist in a Xenograft Mouse Model of Inflammatory Breast Cancer," *Clin. Exp. Metastasis* 27:233-240, Mar. 2010.

Ueda et. al., "Structure-Activity Relationships of Cyclic Peptide-Based Chemokine Receptor CXCR4 Antagonists: Disclosing the Importance of Side-Chain and Backbone Functionalities," *J. Med. Chem.* 50:192-198, 2007.

Wai, "Blockade of Chemokine (C-X-C motif) Receptor 4 for the Inhibition of Hepatocellular Carcinoma Metastasis," *A Thesis, in partial fulfillment of requirements for Ph.D. Degree at the Univ. of Hong Kong*, Jun. 2008.

Zhan et al., "Discovery of Small Molecule CXCR4 Antagonists," *J. Med. Chem.* 50:5655-5664, 2007.

Corson, Timothy W. et al., "Design and Applications of Bifunctional Small Molecules: Why Two Heads Are Better Than One," *ACS Chemical Biology* 3(11):677-692, Nov. 2008.

Daoudi, Jean-Michel et al., "New bicyclam-GalCer analogue conjugates: synthesis and in vitro anti-HIV activity," *Bioorg. & Med. Chem. Letters* 14:495-498, 2004.

Dittmar, Thomas et al., "Adhesion Molecules and Chemokines: the Navigation System for Circulating Tumor (Stem) Cells to Metastasize in an Organ-Specific Manner," *Clin. Exp. Metastasis* 25:11-32, 2008.

Edwards, W. Barry et al., "Generally Applicable, Convenient Solid-Phase Synthesis and Receptor Affinities of Octreotide Analogs," *J. Med. Chem.* 37:3749-3757, 1994.

Ikeuchi, Yoshihiro et al., "Synthesis and Antitumor Activities of Novel 5-Deazaflavin-Sialic Acid Conjugate Molecules," *Bioorg. & Med. Chem.* 8:2027-2035, 2000.

Matsuda, Masao et al., "Heterobifunctional Ligands: Practical Chemoenzymatic Synthesis of a Cell Adhesive Glycopeptide That Interacts With Both Selectins and Integrins," *J. Med. Chem.* 44:715-724, 2001.

Sipkins, Dorothy A. et al., "In Vivo Imaging of Specialized Bone Marrow Endothelial Microdomains for Tumor Engraftment," *Nature Pub. Group GB* 435 (7044):969-973, Jun. 2005.

Takahashi, Takashi et al., "Design and Synthesis of a Water-Soluble Taxol Analogue : Taxol-Sialyl Conjugate," *Bioorg. & Med. Chem. Letters* 8:113-116, 1998.

* cited by examiner

HETEROBIFUNCTIONAL INHIBITORS OF E-SELECTINS AND CXCR4 CHEMOKINE RECEPTORS

CROSS REFERENCE TO RELATED APPLICATION

This application claims the benefit under 35 U.S.C. §119(e) of U.S. Provisional Patent Application No. 61/174,580 filed May 1, 2009, which application is incorporated herein by reference in its entirety.

BACKGROUND

1. Technical Field

The present invention relates generally to compounds, compositions and methods for treating cancer and inflammatory diseases, and for enhancing retention of cells after releasing into circulating blood. More specifically, the present invention relates to heterobifunctional compounds that inhibit E-selectins and CXCR4 chemokine receptors, and uses thereof.

2. Description of the Related Art

A number of cancers are highly treatable when treated before the cancer has moved beyond the primary site. However, often once the cancer has spread beyond the primary site, the treatment options are limited and the survival statistics decline dramatically. Bones are a common location for cancer to infiltrate once leaving the primary tumor location. Breast and prostate cancer are examples of cancers that migrate to bones. Even leukemic cells that arise in the bloodstream may home to the bone marrow. Once cancer resides in bone, it is frequently a cause of pain to the individual. Further, once in the bone marrow, the cancer cells may also become resistant to chemotherapy. In addition, if the particular bone affected is a source for production of blood cells in the bone marrow, the individual may develop a variety of blood cell related disorders. Thus, it is desirable to prevent cancer cells from leaving the primary site, or to prevent extravasation of cancer cells from the bloodstream and infiltration into other tissues. Retention of cancer cells in the bloodstream makes the cells more susceptible to treatment, such as chemotherapy.

Some cancers originate all or in part in bone. For such cancers, it is desirable to mobilize cancer cells from bone to the bloodstream and to prevent those cells (as well as any cancer cells already in the bloodstream) from homing to bone or otherwise leaving the bloodstream. Retention of cancer cells in the bloodstream (or mobilization of cancer cells into the bloodstream and then retention therein) makes the cells more susceptible to treatment, such as chemotherapy.

Hematopoietic stem cells (HSCs) also reside in the bone marrow and are a source of material for cellular therapy. HSCs adhere to the stroma within the bone marrow and in order to be harvested must break these adhesions and mobilize out of the bone marrow. It is desirable to have improved agents to increase the HSCs available for harvesting. Such HSCs are useful for engraftment.

Accordingly, there is a need in the art for the treatment of cancers that may leave the primary site and cancers that originate all or in part in bone, and for improved methods to aid in the preparation of therapeutic-grade stem cells. The present invention fulfills these needs and further provides other related advantages.

BRIEF SUMMARY

Briefly stated, compounds, compositions and methods for treating diseases and for improving methods in which an E-selectin and a CXCR4 chemokine receptor play a role, are provided. In the present invention, the compounds are heterobifunctional compounds wherein an E-selectin inhibitor is linked to a CXCR4 chemokine receptor inhibitor. Such compounds may be combined with a pharmaceutically acceptable carrier or diluent to form a pharmaceutical composition. The compounds may be used to treat cancer in which the cancer cells may leave the primary site, or to treat an inflammatory disease in which the adhesion or migration of cells occurs in the disease, or to release cells such as stem cells (e.g., bone marrow progenitor cells) into circulating blood and enhance retention of the cells in the blood (e.g., to mobilize cells out of bone marrow and maintain the cells in the peripheral bloodstream).

The present invention provides a heterobifunctional compound for inhibition of E-selectin and the CXCR4 chemokine receptor, comprising E-selectin inhibitor-Linker-CXCR4 chemokine receptor inhibitor, or a physiologically acceptable salt thereof.

In one embodiment of the compound, the E-selectin inhibitor consists of:

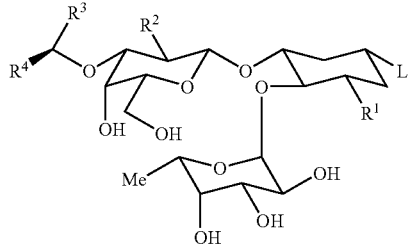

wherein:
L=end of bond to Linker;
$R^1$=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)OX, alkanyl substituted with C(=O)OX, C(=O)NHX, alkanyl substituted with C(=O)NHX, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)X, OX, NHX, NHC(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH;
$R^2$=—OH,

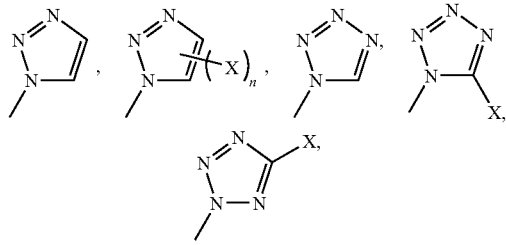

—O—C(=O)—X, —NH$_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

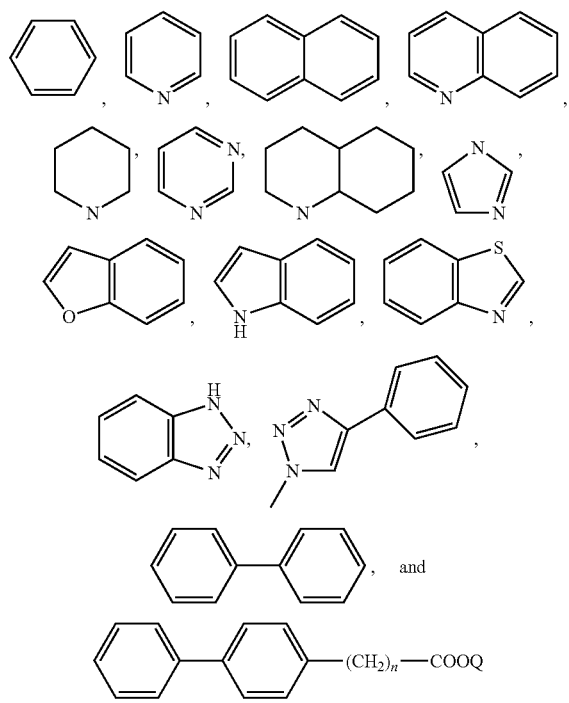

where Q is H or a physiologically acceptable salt, $C_1$-$C_8$ alkanyl, $C_1$-$C_8$ alkenyl, $C_1$-$C_8$ alkynyl, aryl, $(CH_2)_m$-aryl where m is 1-10, and where n=0-10, and any of the above ring compounds may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl, $C_1$-$C_{14}$ aryl, or OY, C(=O)OY, $NY_2$ or C(=O)NHY where Y is H, $C_1$-$C_8$ alkanyl, $C_1$-$C_8$ alkenyl, $C_1$-$C_8$ alkynyl, or $C_1$-$C_{14}$ aryl;

$R^3$=H, $C_1$-$C_8$ alkanyl, $C_1$-$C_8$ alkenyl, $C_1$-$C_8$ alkynyl, CN, $CH_2CN$, C(=O)X where X is H, $C_1$-$C_8$ alkanyl, $C_1$-$C_8$ alkenyl, $C_1$-$C_8$ alkynyl, NHOH, $NHOCH_3$, NHCN, or $NX_2$, or C(=O)OY where Y is H, $C_1$-$C_8$ alkanyl, $C_1$-$C_8$ alkenyl or $C_1$-$C_8$ alkynyl; and $R^4$ = where the cyclopropane ring may be substituted with one to two, and the cyclohexane ring may be substituted with one to three, independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl.

In one embodiment of the compound, the E-selectin inhibitor consists of:

wherein L=end of bond to Linker.

In one embodiment of the compound, the E-selectin inhibitor consists of:

wherein L=end of bond to Linker.

In one embodiment of the compound, the E-selectin inhibitor consists of:

wherein L=end of bond to Linker.

In one embodiment of the compound, the E-selectin inhibitor consists of:

wherein L=end of bond to Linker.

In one embodiment of the compound, the CXCR4 chemokine receptor inhibitor consists of:

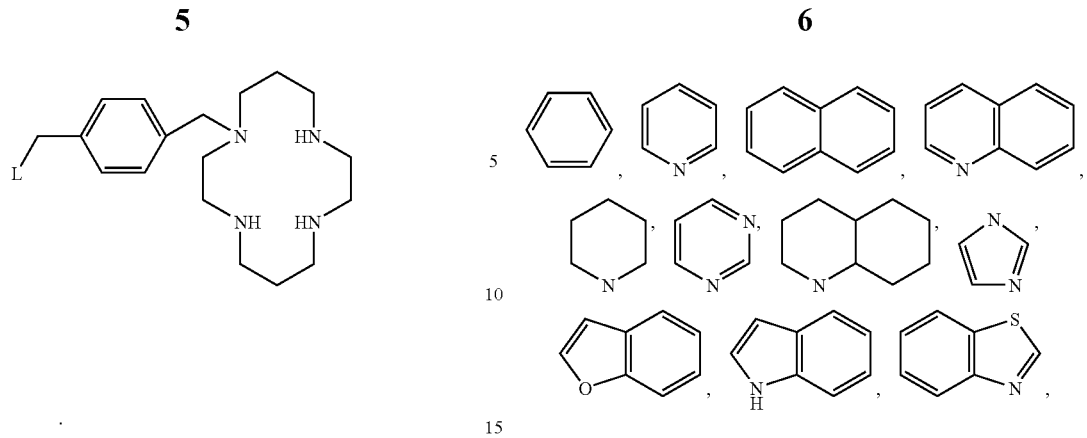

wherein L=end of bond to Linker.

In one embodiment, the compound has the formula:

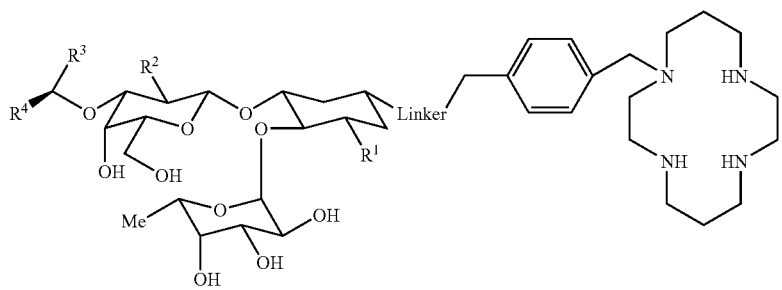

wherein:

R¹=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)OX, alkanyl substituted with C(=O)OX, C(=O)NHX, alkanyl substituted with C(=O)NHX, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)X, OX, NHX, NHC(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH:

R²=—OH,

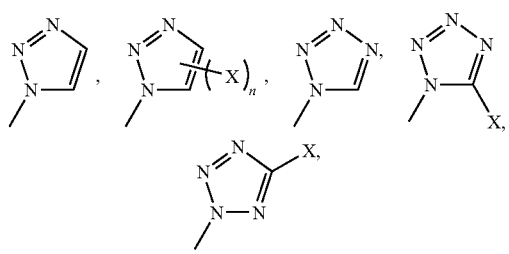

—O—C(=O)—X, —NH₂, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl, -continued

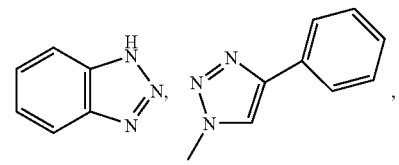

Q is H or a physiologically acceptable salt, $C_1$-$C_8$ alkanyl, $C_1$-$C_8$ alkenyl, $C_1$-$C_8$ alkynyl, aryl, $(CH_2)_m$-aryl where m is 1-10, and where n=0-10, and any of the above ring compounds may be substituted with one to three independently selected of Cl, F, CF₃, $C_1$-$C_8$ alkoxy, NO₂, $C_1$-$C_8$ alkanyl, $C_1$-$C_8$ alkenyl, $C_1$-$C_8$ alkynyl, $C_1$-$C_{14}$ aryl, or OY, C(=O)OY, NY₂ or C(=O)NHY where Y is H, $C_1$-$C_8$ alkanyl, $C_1$-$C_8$ alkenyl, $C_1$-$C_8$ alkynyl, or $C_1$-$C_{14}$ aryl;

R³=H, $C_1$-$C_8$ alkanyl, $C_1$-$C_8$ alkenyl, $C_1$-$C_8$ alkynyl, CN, CH₂CN, C(=O)X where X is H, $C_1$-$C_8$ alkanyl, $C_1$-$C_8$ alkenyl, $C_1$-$C_8$ alkynyl, NHOH, NHOCH₃, NHCN, or NX₂, or C(=O)OY where Y is H, $C_1$-$C_8$ alkanyl, $C_1$-$C_8$ alkenyl or $C_1$-$C_8$ alkynyl; and R⁴ = 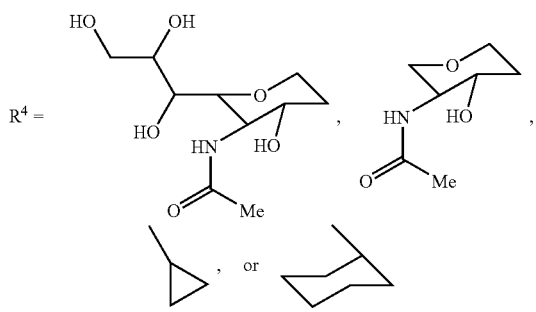

where the cyclopropane ring may be substituted with one to two, and the cyclohexane ring may be substituted with one to three, independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl.

In one embodiment, the compound has the formula:

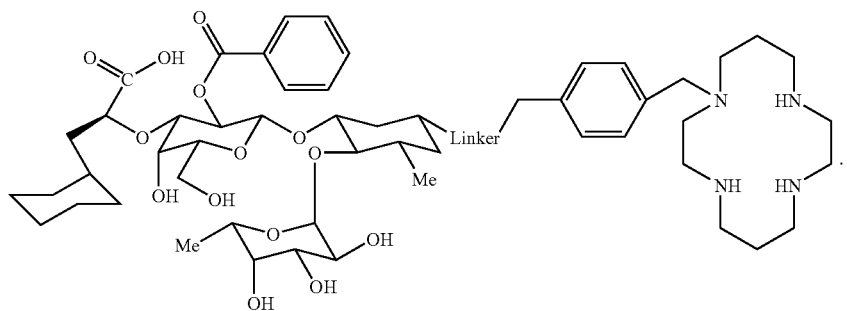

In one embodiment, the compound has the formula:

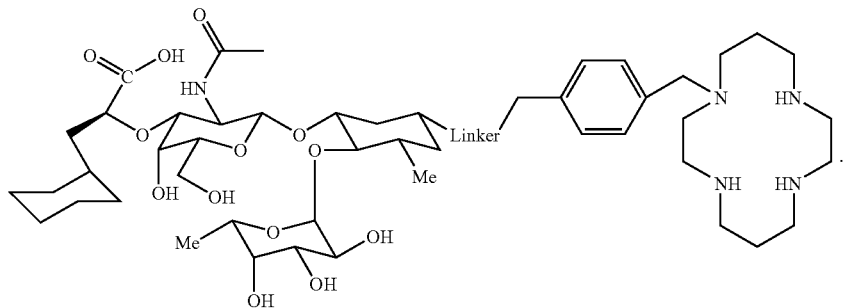

In one embodiment, the compound has the formula:

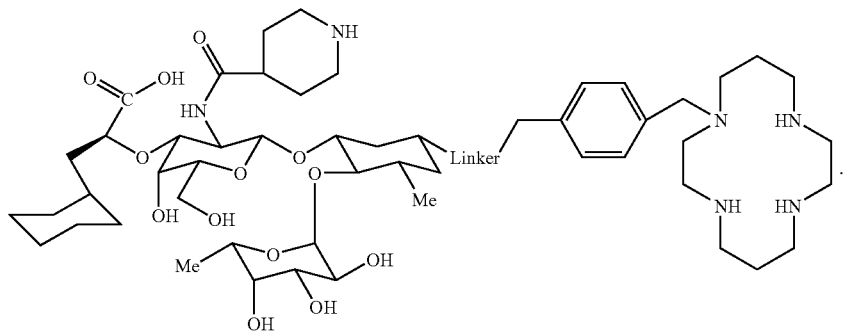

In one embodiment, the compound has the formula:

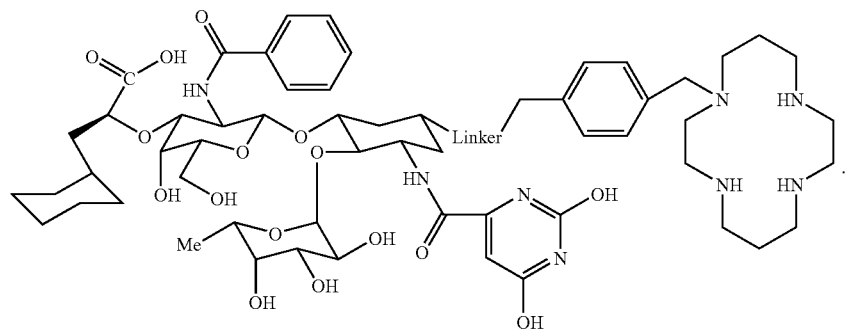

In one embodiment, the Linker of the compound is —C(=O)—NH—(CH$_2$)$_2$—NH—.

In one embodiment, the Linker of the compound is —CH$_2$—NH—CH$_2$—.

In one embodiment, the Linker of the compound is —C(=O)—NH—CH$_2$—.

These linkers, as well as the others disclosed herein and those otherwise known in the art, are for use in a compound of the present invention such as the four embodiments depicted above containing a Linker.

The present invention provides a method for the treatment of a cancer in which the cancer cells may leave the primary site in an individual who is in need of such treatment, comprising administering to the individual a compound of the present invention in an amount effective for treatment, wherein the compound is with or without a pharmaceutically acceptable carrier or diluent.

The present invention provides a method for the treatment of a cancer in which it is desired to mobilize cancer cells from a site into the bloodstream and retain the cancer cells in the bloodstream in an individual who is in need of such treatment, comprising administering to the individual a compound of the present invention in an amount effective for treatment, wherein the compound is with or without a pharmaceutically acceptable carrier or diluent.

The present invention provides a method for releasing cells into circulating blood and enhancing retention of the cells in the blood of an individual who is need of such treatment, comprising administering to the individual a compound of the present invention in an amount effective for treatment, wherein the compound is with or without a pharmaceutically acceptable carrier or diluent. In an embodiment, the method further includes the step of collecting the cells released. In an embodiment, the step of collecting utilizes apheresis. In an embodiment, the cells are stem cells (e.g., bone marrow progenitor cells). In an embodiment, G-CSF is administered to the individual.

The present invention provides a method for the treatment of an inflammatory disease in which the adhesion or migration of cells occurs in the disease in an individual in need of such treatment, comprising administering to the individual a compound of the present invention in an amount effective for treatment, wherein the compound is with or without a pharmaceutically acceptable carrier or diluent.

The present invention provides a pharmaceutical composition comprising a compound of the present invention and a pharmaceutically acceptable carrier or diluent.

In other embodiments, the above compounds thereof may be used in the manufacture of a medicament, and for any of the uses recited herein.

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1A:
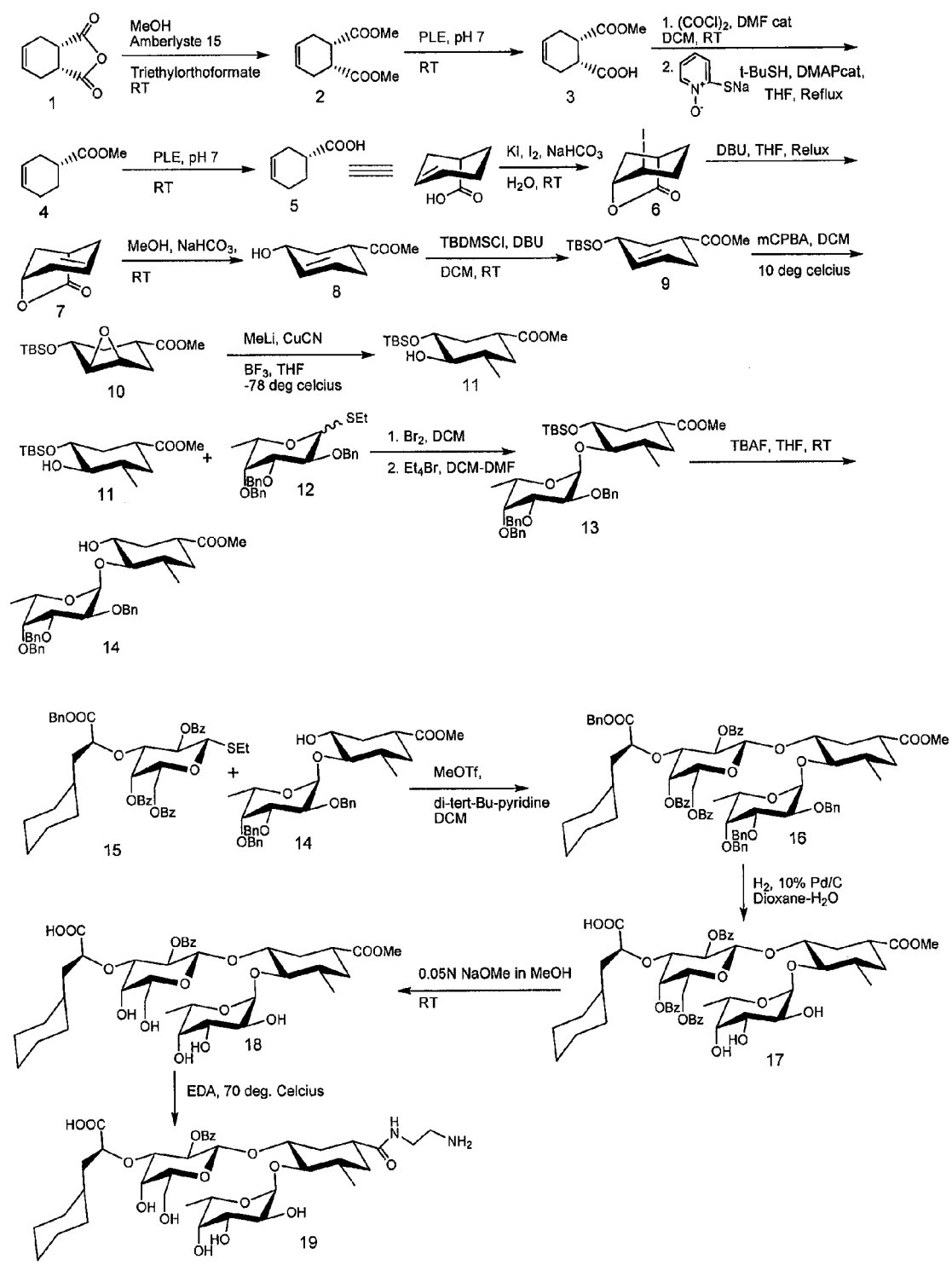
FIG. 1 (FIG. 1A and FIG. 1B) is a diagram illustrating the synthesis of heterobifunctional Compound #1 (compound 27).

As noted above, the present invention provides compounds, compositions and methods for treating diseases in which an E-selectin and a CXCR4 chemokine receptor play a role, and for enhancing retention of cells after releasing into circulating blood. The compounds have a variety of uses in vitro and in vivo.

As used herein, the term "E-selectin inhibitor" refers to an inhibitor of E-selectin only, as well as to an inhibitor of E-selectin and either P-selectin or L-selectin, or E-selectin and both P-selectin and L-selectin. Thus, there is E-selectin inhibition regardless of whether there is also inhibition of either P-selectin or L-selectin or both P-selectin and L-selectin.

All compounds of the present invention or useful thereto (e.g., for pharmaceutical compositions or methods of treating) include physiologically acceptable salts thereof. Examples of such salts are Na, K, Li, Mg, Ca, and Cl.

A compound of the present invention is a heterobifunctional compound wherein an E-selectin inhibitor is linked (i.e., covalently bonded) to a CXCR4 chemokine receptor inhibitor. Such a compound comprises, or consists of, the formula:

E-selectin inhibitor-Linker-CXCR4 chemokine receptor inhibitor. Accordingly, the compound functions to inhibit E-selectin and to inhibit the CXCR4 chemokine receptor.

E-selectin inhibitors are well known in the art. Some E-selectin inhibitors are specific for E-selectin only. Other E-selectin inhibitors have the ability to inhibit not only E-selectin but additionally P-selectin or L-selectin or both P-selectin and L-selectin. Examples of E-selectin inhibitors (specific for E-selectin or otherwise) are disclosed in U.S. Pat. No. 7,060,685; U.S. Application Publication No. US-2007-0054870; U.S. Application Publication No. US-2008-0161546; and references cited in any of these patent or published application documents. Those examples are small organic molecules. Other known E-selectin inhibitors are amino acid-based, such as antibodies. For example, the humanized monoclonal antibody CDP850 is an E-selectin inhibitor.

In one embodiment of the compound, the E-selectin inhibitor consists of:

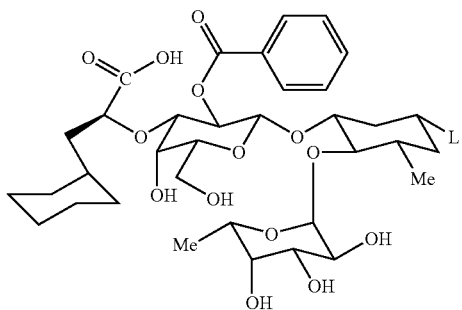

wherein L=end of bond to Linker.

In one embodiment of the compound, the E-selectin inhibitor consists of:

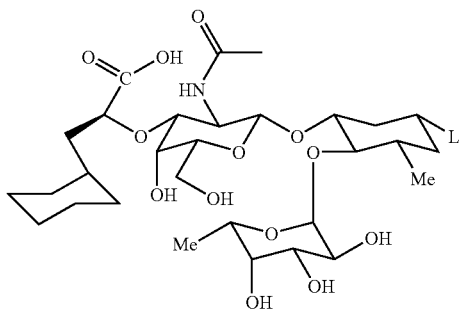

wherein L=end of bond to Linker.

In one embodiment of the compound, the E-selectin inhibitor consists of:

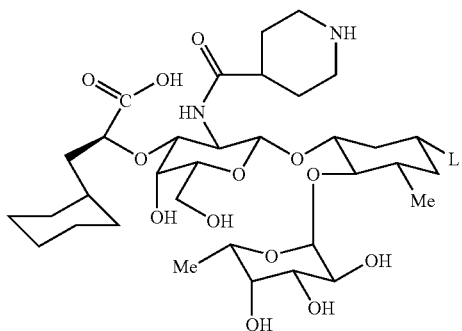

wherein L=end of bond to Linker.

In one embodiment of the compound, the E-selectin inhibitor consists of:

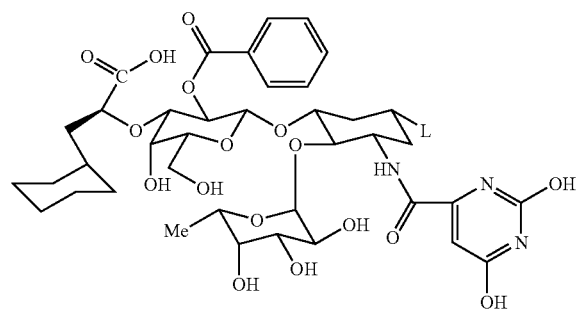

wherein L=end of bond to Linker.

CXCR4 chemokine receptor inhibitors are well known in the art. Such inhibitors will typically prevent the binding of stromal derived factor-1 (SDF-1) to a CXCR4 receptor. Examples of CXCR4 chemokine receptor inhibitors are AMD-3100 (Hendrix et al., Antimicrob. Agents Chemother. 44:1667-1673, 2000); ALX40-4C (Doranz et al., AIDS Research and Human Retroviruses 17:475-486, 2001); and T134 (Arakaki et al., J. Virol. 73:1719-1723, 1999). These examples include a small organic molecule and amino acid-based molecules, such as the T22 peptide. AMD-3100 is a bicyclam. Each of the two cyclam rings is attached to the same phenyl ring (each cyclam ring is para to the other) via a methylene group. In one embodiment of a compound of the present invention, the CXCR4 chemokine receptor inhibitor is a phenyl ring to which is attached only one cyclam ring.

In a compound of the present invention, an E-selectin inhibitor and a CXCR4 chemokine receptor inhibitor are covalently joined via a linker (i.e., interposed between the two inhibitors is a "Linker"). A linker may be (or may include) a spacer group, such as —(CH$_2$)$_p$— or —O(CH$_2$)$_p$— where p is generally about 1-20 (including any whole integer range therein). Other examples of spacer groups include a carbonyl or carbonyl containing group such as an amide. An embodiment of such spacer groups is

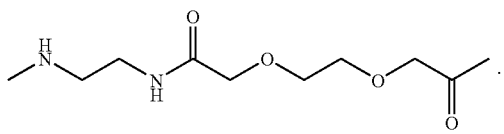 [SMILES: CNCCNC(=O)COCCOCC(C)=O]

Embodiments of linkers include the following:

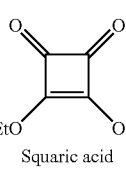 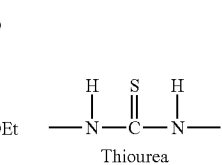 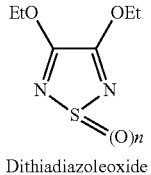

Squaric acid     Thiourea     Dithiadiazoleoxide

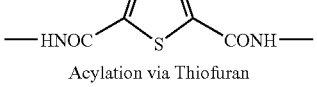

Acylation via Thiofuran

-continued

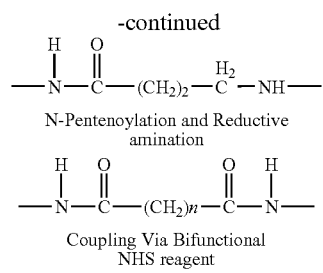
N-Pentenoylation and Reductive amination

—N(H)—C(=O)—(CH₂)ₙ—C(=O)—N(H)—
Coupling Via Bifunctional NHS reagent

Other linkers, e.g., polyethylene glycols (PEG) or —C(=O)—NH—(CH₂)$_p$—C(=O)—NH₂ where p is as defined above, will be familiar to those in the art or in possession of the present disclosure.

In another embodiment, the linker is

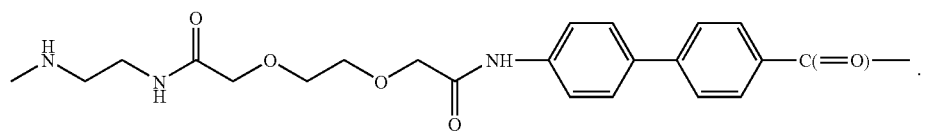

In another embodiment, the linker is

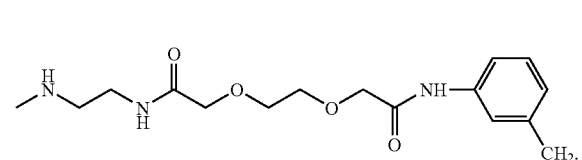

In another embodiment, the linker is —C(=O)—NH—(CH₂)₂—NH—.

In another embodiment, the linker is —CH₂—NH—CH₂—.

In another embodiment, the linker is —C(=O)—NH—CH₂—.

In one embodiment of a compound of the present invention, the E-selectin inhibitor consists of:

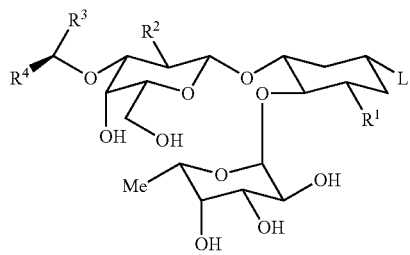

wherein L is the end of the bond to Linker.

In the present disclosure, there are several chemical abbreviations. "Me" is methyl. "Et" is ethyl. "Ar" is aryl. "Bz" is benzoyl.

Selection of a substituent at $R^1$ includes H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)OX, alkanyl substituted with C(=O)OX, C(=O)NHX, alkanyl substituted with C(=O)NHX, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)X, OX, NHX, NHC(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH.

Selection of a substituent at $R^2$ includes —OH,

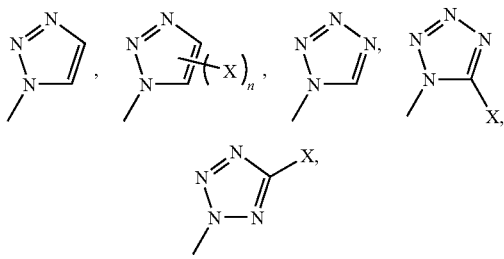

—O—C(=O)—X, —NH₂, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

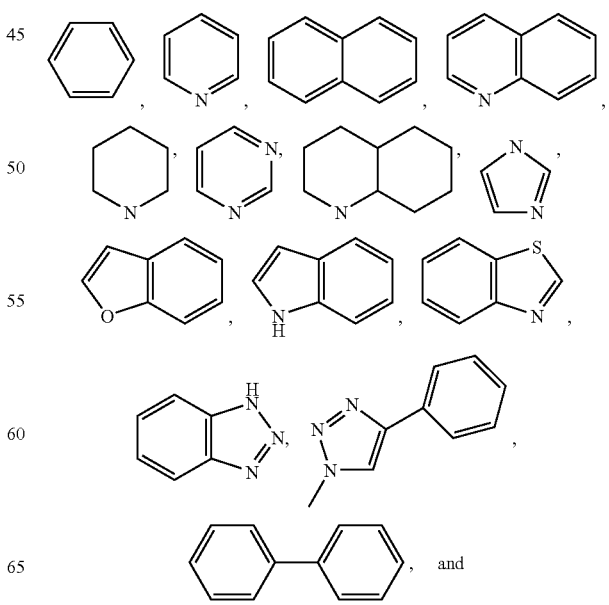

and

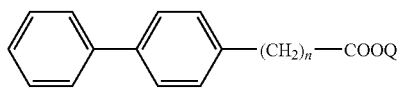

where Q is H or a physiologically acceptable salt, $C_1$-$C_8$ alkanyl, $C_1$-$C_8$ alkenyl, $C_1$-$C_8$ alkynyl, aryl, $(CH_2)_m$-aryl where m is 1-10, and where n=0-10, and any of the above ring compounds may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl, $C_1$-$C_{14}$ aryl, or OY, C(=O)OY, $NY_2$ or C(=O)NHY where Y is H, $C_1$-$C_8$ alkanyl, $C_1$-$C_8$ alkenyl, $C_1$-$C_8$ alkynyl, or $C_1$-$C_{14}$ aryl.

Selection of a substituent at $R^3$ includes H, $C_1$-$C_8$ alkanyl, $C_1$-$C_8$ alkenyl, $C_1$-$C_8$ alkynyl, CN, $CH_2CN$, C(=O)X where X is H, $C_1$-$C_8$ alkanyl, $C_1$-$C_8$ alkenyl, $C_1$-$C_8$ alkynyl, NHOH, $NHOCH_3$, NHCN, or $NX_2$, or C(=O)OY where Y is H, $C_1$-$C_8$ alkanyl, $C_1$-$C_8$ alkenyl or $C_1$-$C_8$ alkynyl; and Selection of a substituent at $R^4$ includes

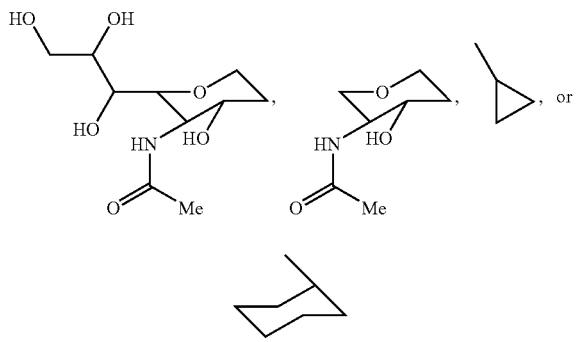

where the cyclopropane ring may be substituted with one to two, and the cyclohexane ring may be substituted with one to three, independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl.

As used herein, a "$C_1$-$C_8$ alkanyl" refers to an alkane substituent with one to eight carbon atoms and may be straight chain, branched or cyclic (cycloalkanyl). Examples are methyl, ethyl, propyl, isopropyl, butyl and t-butyl. A "halogenated $C_1$-$C_8$ alkanyl" refers to a "$C_1$-$C_8$ alkanyl" possessing at least one halogen. Where there is more than one halogen present, the halogens present may be the same or different or both (if at least three present). A "$C_1$-$C_8$ alkenyl" refers to an alkene substituent with one to eight carbon atoms, at least one carbon-carbon double bond, and may be straight chain, branched or cyclic (cycloalkenyl). Examples are similar to "$C_1$-$C_8$ alkanyl" examples except possessing at least one carbon-carbon double bond. A "$C_1$-$C_8$ alkynyl" refers to an alkyne substituent with one to eight carbon atoms, at least one carbon-carbon triple bond, and may be straight chain, branched or cyclic (cycloalkynyl). Examples are similar to "$C_1$-$C_8$ alkanyl" examples except possessing at least one carbon-carbon triple bond. An "alkoxy" refers to an oxygen substituent possessing a "$C_1$-$C_8$ alkanyl," "$C_1$-$C_8$ alkenyl" or "$C_1$-$C_8$ alkynyl." This is —O-alkyl; for example methoxy, ethoxy, n-propoxy, i-propoxy, n-butoxy and the like; and alkenyl or alkynyl variations thereof (except for methoxy). It further refers to the group O-alkyl-W-alkyl where W is O or N; for example —O—$(CH_2)_n$—W—$(CH_2)_m$ where n and m are independently 1-10. An "aryl" refers to an aromatic substituent with one to fourteen carbon atoms as ring atoms in one or multiple rings which may be separated by a bond or fused. As used herein, "aryl" includes "heteroaryl." A "heteroaryl" is similar to an "aryl" except the aromatic substituent possesses at least one heteroatom (such as N, O or S) in place of a ring carbon. Where an aromatic substituent is an aryl in which all the ring atoms are carbon (i.e., not a heteroaryl), there are typically six to fourteen ring atoms. Where an aryl is a heteroaryl, there may be less than six carbon ring atoms. Examples of aryls include phenyl, naphthyl, pyridinyl, pyrimidinyl, triazolo, furanyl, oxazolyl, thiophenyl, quinolinyl and diphenyl.

In one embodiment of a compound of the present invention, the CXCR4 chemokine receptor inhibitor consists of:

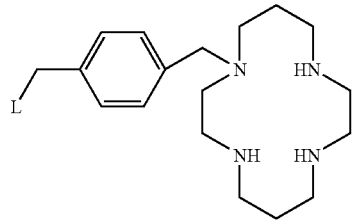

wherein L is the end of the bond to Linker.

In one embodiment, the compound has the formula:

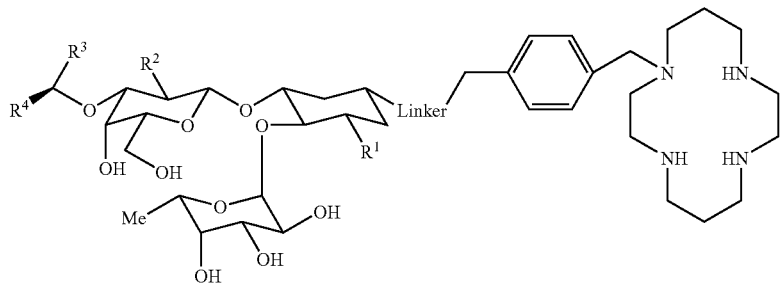

wherein $R^1$, $R^2$, $R^3$ and $R^4$ are as defined above.

In one embodiment in which the linker is —C(=O)—NH—(CH₂)₂—NH—, the compound has the formula:

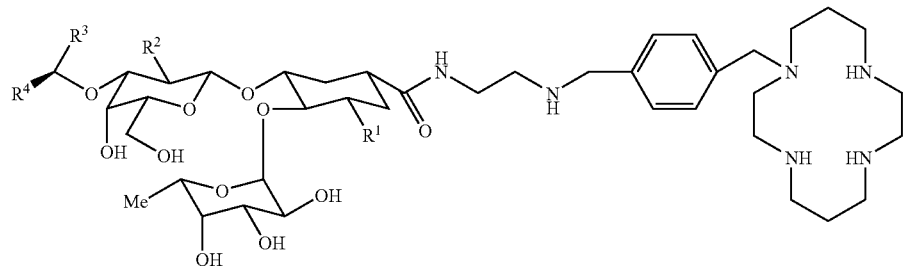

wherein R¹, R², R³ and R⁴ are as defined above.

In one embodiment in which the linker is —CH₂—NH—CH₂—, the compound has the formula:

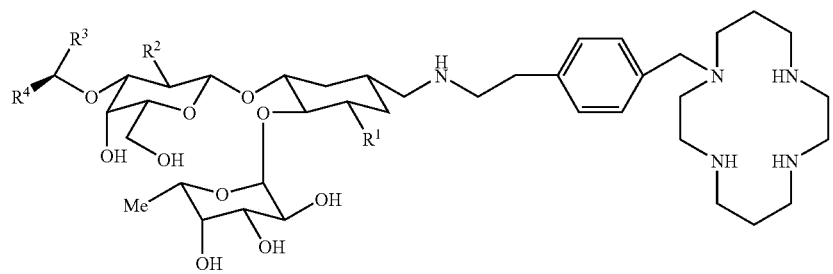

wherein R¹, R², R³ and R⁴ are as defined above.

In one embodiment in which the linker is —C(=O)—NH—CH₂—, the compound has the formula:

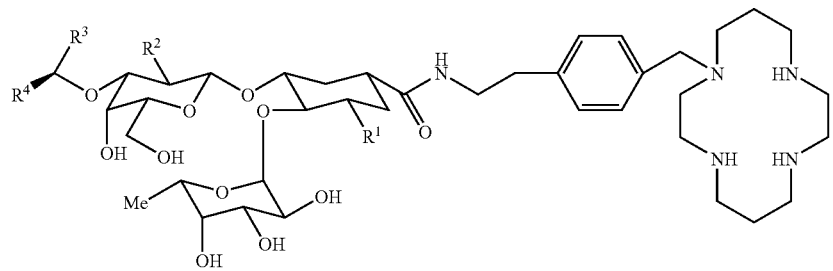

wherein R¹, R², R³ and R⁴ are as defined above.

In one embodiment in which the linker is —C(=O)—NH—(CH₂)₂—NH—, the compound has the formula:

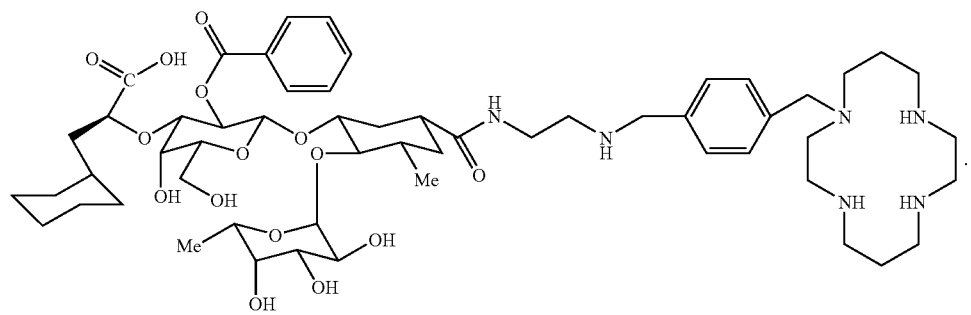 [SMILES: CC1CC(C(=O)NCCNCc2ccc(CN3CCCNCCNCCCNCC3)cc2)CC(OC2OC(CO)C(O)C(O[C@@H](CC3CCCCC3)C(=O)O)C2OC(=O)c2ccccc2)C1OC1OC(C)C(O)C(O)C1O]

50

In one embodiment in which the linker is —CH₂—NH—CH₂—, the compound has the formula:

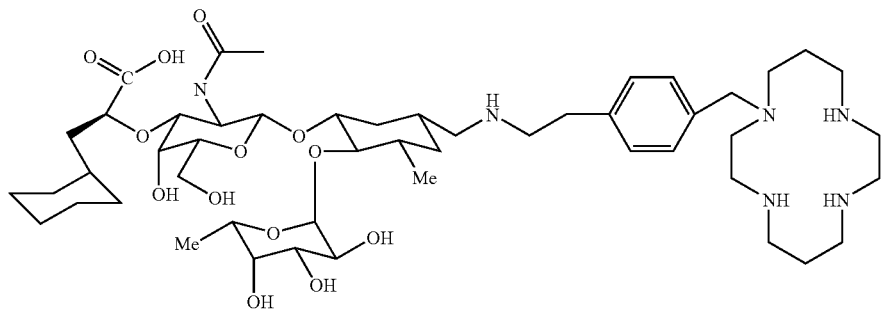

In one embodiment in which the linker is —C(=O)—NH—CH₂—, the compound has the formula:

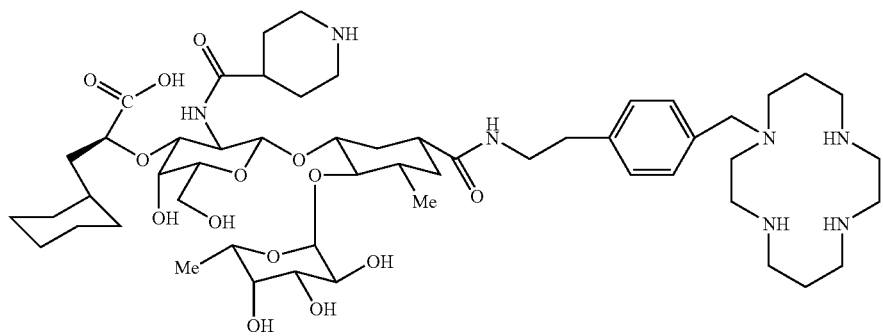

In one embodiment in which the linker is —C(=O)—NH—(CH₂)₂—NH—, the compound has the formula:

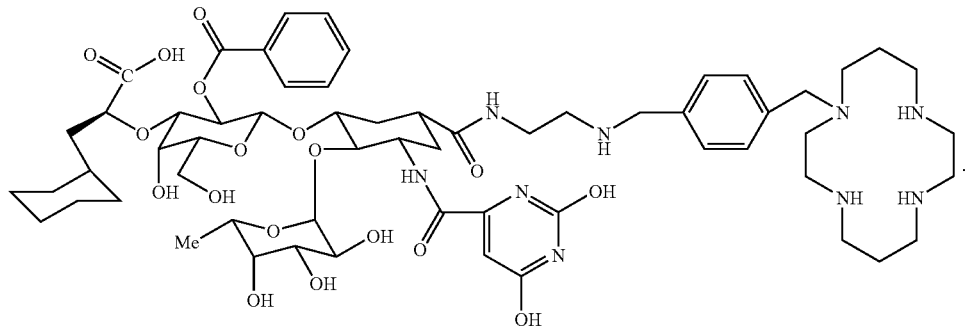 [SMILES: CC1OC(OC2C(NC(=O)c3cc(O)nc(O)n3)CC(C(=O)NCCNCc3ccc(CN4CCCNCCNCCCNCC4)cc3)CC2OC2OC(CO)C(O)C(O[C@@H](CC3CCCCC3)C(=O)O)C2OC(=O)c2ccccc2)C(O)C(O)C1O]

All compounds of the present invention or useful thereto (e.g., for pharmaceutical compositions or methods of treating), include physiologically acceptable salts thereof. Examples of such salts are Na, K, Li, Mg, Ca and Cl.

Compounds as described herein may be present within a pharmaceutical composition. A pharmaceutical composition comprises one or more compounds in combination with (i.e., not covalently bonded to) one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of compound release. The amount of compound contained within a sustained release formulation depends upon the site of implantation, the rate and expected duration of release and the nature of the condition to be treated or prevented.

The above-described compounds including equivalents thereof are useful in methods of the present invention. In one embodiment, the compounds may be used in a method for the treatment of a cancer in which the cancer cells may leave the primary site. A primary site may be, for example, solid tissue (e.g., breast or prostate) or the bloodstream. An individual who is in need of such treatment is administered at least one (i.e., one or more) of the above-described compounds in an amount effective for the treatment. In addition to breast cancer and prostate cancer, other examples of infiltrating diseases include lung cancer and melanoma, as well as the hematological malignancies (e.g., leukemias and myelomas). As used herein, the term "treatment" (including variations such as "treating") includes for the disease or a complication associated with the disease, and includes prevention. For example, a complication associated with the cancer may not have presented itself in an individual with the disease, and a compound may be administered to prevent presentation of the complication in the individual. Complications associated with a cancer in which the cancer cells may leave the primary site include, for example, metastasis and infiltration of cancer cells to other tissues. For example, acute myelogenous leukemia (AML) and multiple myeloma (MM) cells migrate to the endosteal region of the bone marrow where the cells become quiescent and are protected from chemotherapy-induced apoptosis. Administration of a compound described herein may prevent adhesion or migration of cancer cells. Such prevention can result in making the cancer cells more susceptible to treatment with chemotherapy. Administration of a compound described herein in the context of prevention may be to an individual who is at risk of occurrence of a cancer for the first time, or for recurrence of a cancer. For example, while a brain cancer such as glioblastoma multiforme is typically treated with another type of therapy (such as radiation or chemotherapy) for the first occurrence, such therapy is usually not effective to prevent recurrence.

The term "treatment" as used herein refers to any of a variety of positive effects from the treatment including, for example, eradicating a complication associated with the disease, relieving to some extent a complication, slowing or stopping progression of the disease, enhancing the effectiveness of one or more therapies for the disease, and prolonging the survival time of the recipient. The treatment may be used in conjunction with one or more other therapies for a cancer or a complication associated therewith.

In another embodiment, the above-described compounds including equivalents may be used in a method for the treatment of a cancer in which it is desired to mobilize cancer cells from a site into the bloodstream and retain the cancer cells in the bloodstream. An individual who is in need of such treatment is administered at least one (i.e., one or more) of the compounds in an amount effective for the treatment. Examples of cancers for such treatment include leukemias and myelomas (e.g., AML and MM). Mobilizing cancer cells into the bloodstream from a site and retaining the cells therein can result in making the cancer cells more susceptible to treatment with chemotherapy. An example of a site from which to mobilize cancer cells is bone. Cancer cells may, for example, be in circulation and then home to bone. Once in bone, the cancer cells are protected from chemotherapy. A compound described herein may be used, for example, to mobilize cancer cells from bone into the bloodstream and prevent cancer cells from homing to bone, thereby retaining the cancer cells in the bloodstream. Administration of a compound described herein in the context of prevention may be to an individual who is at risk of occurrence of a cancer for the first time, or for recurrence of a cancer. For example, while a brain cancer such as glioblastoma multiforme is typically treated with another type of therapy (such as radiation or chemotherapy) for the first occurrence, such therapy is usually not effective to prevent recurrence.

In another embodiment, the above-described compounds including equivalents may be used in a method for releasing cells (such as hematopoietic stem cells) into circulating blood and enhancing retention of the cells in the blood. An individual who is in need of such treatment is administered at least one (i.e., one or more) of the compounds in an amount effective for the treatment. One use of the method is, for example, for stem cell harvesting. Stem cells may be needed, for example, after high-dose chemotherapy treatment. Many chemotherapies suppress bone marrow which disrupts the production of certain components of blood in an individual. As a result, the individual may develop a variety of blood cell related disorders and continuation of chemotherapy may be compromised. A compound described herein may be used, for example, to release stem cells into circulating blood and enhance retention of the stem cells in the blood. The method may include a further step of collecting cells that are released. For example, released stem cells may be collected. A variety of techniques are known in the art for collecting cells. For example, apheresis may be utilized. An example of a stem cells is a bone marrow progenitor cell. The release of such cells from bone marrow into circulating blood and retention therein has a variety of uses. For example, the mobilized bone marrow progenitor cells may be collected from the blood. A use of such collected cells is to obtain healthy bone marrow progenitor cells from an individual prior to treatment of the individual in a manner such that bone marrow is suppressed. Following treatment, the individual can receive a bone marrow transplantation utilizing the bone marrow progenitor cells collected prior to treatment. This is useful, for example, where an individual needs to be subjected to a chemotherapy protocol that will suppress bone marrow.

It can be desirable to additionally treat an individual with at least one (i.e., one or more) colony stimulating factor. Such a factor may be administered, for example, before or simultaneous with administration of at least one of the above-described compounds. Where administration is simultaneous, the combination may be administered from a single container or two (or more) separate containers. An example of a suitable colony stimulating factor is granulocyte-colony stimulating factor (G-CSF). G-CSF induces the bone marrow to grow and produce more stem cells. A compound described herein aids in releasing stem cells into circulating blood. Stem cells produced in bone marrow and released into circulating blood, as a result of the combination of the administration (separately or together) of a compound described herein and G-CSF, may be collected as described above. Such collected stem cells may be, for example, administered to the individual after chemotherapy. The stem cells return to the bone marrow and produce blood cells. Application of a compound described herein to mobilization and harvesting of healthy bone marrow progenitor cells from bone marrow treated with G-CSF provides cells useful, for example, for bone marrow transplantation.

In another embodiment, the above-described compounds including equivalents may be used in a method for the treatment of an inflammatory disease in which the adhesion or migration of cells occurs in the disease. An individual who is in need of such treatment is administered at least one (i.e., one or more) of the compounds in an amount effective for the treatment. Example of inflammatory diseases include inflammatory skin disorders such as atopic dermatitis and psoriasis. The treatment may reduce (partially or totally) the disease or a complication associated therewith, such as pain. The treatment may be used in conjunction with one or more other therapies for such an inflammatory disease or a complication associated therewith.

The above-described compounds may be administered in a manner appropriate to the disease to be treated. Appropriate dosages and a suitable duration and frequency of administration may be determined by such factors as the condition of the patient, the type and severity of the patient's disease and the method of administration. In general, an appropriate dosage and treatment regimen provides the compound(s) in an amount sufficient to provide therapeutic or prophylactic benefit. Within particularly preferred embodiments of the invention, a compound may be administered at a dosage ranging from 0.001 to 1000 mg/kg body weight (more typically 0.01 to 1000 mg/kg), on a regimen of single or multiple daily doses. Appropriate dosages may generally be determined using experimental models or clinical trials. In general, the use of the minimum dosage that is sufficient to provide effective therapy is preferred. Patients may generally be monitored for therapeutic effectiveness using assays suitable for the condition being treated, which will be familiar to those of ordinary skill in the art.

At least one (i.e., one or more) of the above-described compounds may be administered in combination with at least one (i.e., one or more) agent, e.g., chemotherapeutic agent or anti-inflammatory agent. In addition, the administration may be in conjunction with one or more other therapies for reducing toxicities of chemotherapy. For example, at least one (i.e., one or more) agent to counteract (at least in part) a side effect of chemotherapy may be administered. At least one compound described herein may be administered before, after or simultaneous with administration of at least one chemotherapeutic agent or anti-inflammatory agent. Where administration is simultaneous, the combination may be administered from a single container or two (or more) separate containers.

The following Examples are offered by way of illustration and not by way of limitation.

Examples

Example 1

Figure 1B:
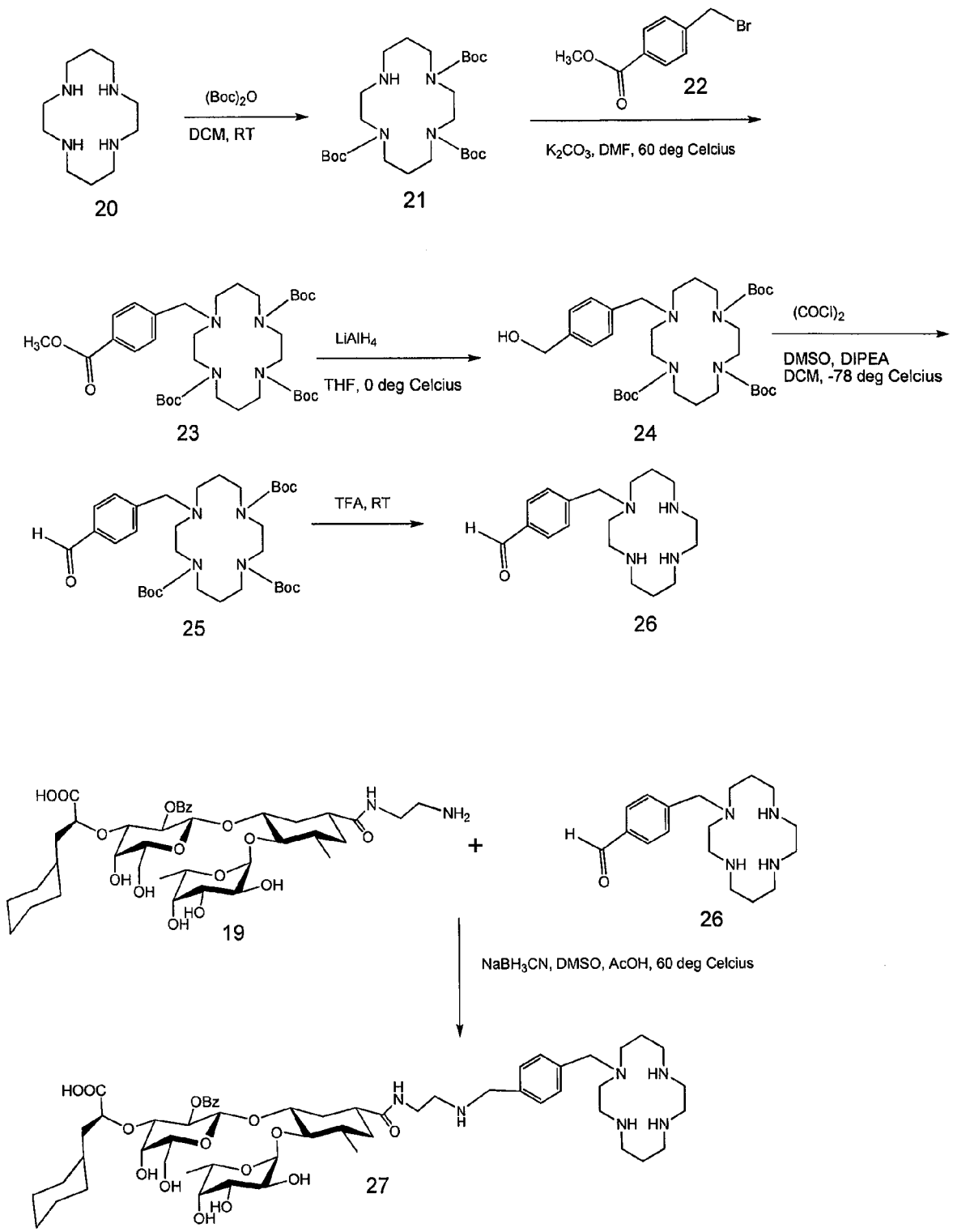

Synthesis of Heterobifunctional Compound #1
(Compound 27 of FIG. 1)

Synthesis of Compound 2:
Commercially available (Aldrich Chemical Co., Milwaukee, Wis.) cis-1,2,3,6-tetrahydrophthalic anhydride (compound 1, 50 g) is added to a suspension of amberlyste 15 (50 g, dried under vacuum) in methanol (1 L) with stirring. Triethylorthoformate (100 ml) is added immediately while stirring. The reaction mixture is then vigorously stirred for 5 days at room temperature and additional triethylorthoformate is added. Stirring is continued for an additional 4 days, then the reaction mixture filtered over celite and washed with methanol. The solvent is removed in vacuum and the residue is dissolved in $CH_2Cl_2$ (200 ml). The solution is washed with a cold saturated solution of $NaHCO_3$ (200 ml) and cold brine (200 ml). The organic layer is dried ($Na_2SO_4$), filtered and concentrated to dryness to afford compound 2 (55 g).

Synthesis of Compound 3:
To a suspension of compound 2 (10 g) in phosphate buffer (400 ml, pH 7) is added PLE (40 mg, 1080 unit). The pH of the mixture is maintained at 7 by continuous dropwise addition of 1M NaOH solution via syringe pump. The reaction is stirred at 20° C. until 1 equivalent of NaOH (50 ml) is used. The reaction mixture is transferred to a reparatory funnel and EtOAc (400 ml) is added. The layers are separated and the organic layer is extracted with phosphate buffer (2×250 ml, pH 7). The combined aqueous layers are acidified (pH 2) with aqueous HCl (1M) and extracted with EtOAc (3×400 ml). The combined organic layers are dried ($Na_2SO_4$), filtered and concentrated to dryness to afford compound 3 (7.8 g).

Synthesis of Compound 4:
To a solution of compound 3 (2 g) in dry $CH_2Cl_2$ (35 ml) is added $(COCl)_2$ (1.4 ml) and DMF (0.025 ml) and stirred for 3 h at RT. The solution is evaporated to dryness (rotavapor is purged with argon). The residue is dissolved in dry THF (40 ml) and is added dropwise over a period of 20 min to a boiling suspension of 2-mercaptopyridine-1-oxide sodium salt (2 g), t-BuSH (6 ml), and 4-DMAP (52 mg) in dry THF (100 ml). The solution is stirred under reflux for 3 h. The reaction mixture is cooled down to RT and transferred into a separatory funnel with EtOAc (100 ml) and washed with $H_2O$ (100 ml). The aqueous layer is extracted with EtOAc (2×200 ml). The combined organic layers are dried ($Na_2SO_4$), filtered and concentrated to dryness. The crude product is purified by column chromatography (silica) to afford compound 4 as yellowish oil (1.1 g).

Synthesis of Compound 5:
To a suspension of compound 4 (4 g) in phosphate buffer (400 ml, pH 7) is added PLE (42 mg) with stirring. The pH is kept at 7 by adding NaOH solution (1M) via syringe pump. The reaction mixture is stirred at RT until 1 equivalent of NaOH is used. The reaction mixture is transferred to a separatory funnel and washed with EtOAc (2×250 ml). The layers are separated and the organic layers are extracted with phosphate buffer (2×250 ml, pH 7). The combined aqueous layers are acidified to pH 2 with aqueous HCl solution and extracted with EtOAc (3×300 ml). The combined organic layers are dried ($Na_2SO_4$), filtered and evaporated to dryness. The crude product is filtered through a short plug of silica to afford compound 5 (3 g).

Synthesis of Compound 6:
Compound 5 (4 g) is suspended in water (90 ml) and cooled down to 0° C. $NaHCO_3$ (8 g) is added followed by a solution of KI (32 g) and $I_2$ (8 g) in water (75 ml). The reaction mixture is stirred at RT for 24 h and then extracted with $CH_2Cl_2$ (3×30 ml). The combined organic layers are washed with a saturated solution of $Na_2S_2O_3$ in water (125 ml). The aqueous layer is extracted with $CH_2Cl_2$ (2×30 ml). The combined organic layers are protected from light, dried ($Na_2SO_4$), filtered, and concentrated to dryness and quickly under high vacuum to afford iodolactone 6 as an off-white solid (7.5 g).

Synthesis of Compound 7:
Compound 6 (7 g) is dissolved in dry THF (170 ml) and DBU (7 ml) is added. The reaction mixture is refluxed for 20 h and then cooled down to RT. Diethyl ether (100 ml) is added and transferred into a separatory funnel and extracted with an aqueous solution of HCl (200 ml, 0.5M). The aqueous layers are extracted with $Et_2O$ (3×100 ml). The combined organic layers are washed with brine (200 ml), dried ($Na_2SO_4$), filtered, and concentrated to dryness. The crude product is purified by column chromatography (silica gel) to afford compound 7 (3.7 g).

Synthesis of Compound 8:

$NaHCO_3$ (2.2 g) is dried under vacuum and then dry MeOH (132 ml) is added with stirring followed by compound 7 (3 g). The reaction mixture is then stirred at RT under argon for 12 h. The solvent is evaporated off and the residue is transferred into a separatory funnel with $CH_2Cl_2$ (35 ml), extracted with water (40 ml), and with brine (40 ml). The aqueous layer is extracted with $CH_2Cl_2$ (2×35 ml). The combined organic layers are dried ($Na_2SO_4$), filtered, and concentrated to dryness to give compound 8 (5 g).

Synthesis of Compound 9:

To a solution of compound 8 (4 g) in dry $CH_2Cl_2$ (80 ml) is added tert-butyldimethylsilyl chloride (7.2 ml) in small portions, followed by DBU (9.5 ml). The reaction mixture is stirred for 12 h and then quenched with MeOH (12 ml). The reaction mixture is transferred into a separatory funnel with $CH_2Cl_2$ (60 ml), washed with cold saturated solution of $NaHCO_3$ (50 ml) and cold brine (50 ml). The aqueous layers are extracted with $CH_2Cl_2$ (2×50 ml). The combined organic layers are dried ($Na_2SO_4$), filtered and concentrated to dryness. The residue is purified by column chromatography (silica) to give compound 9 (6 g).

Synthesis of Compound 10:

To a cold (10° C.) solution of compound 9 (5 g) in $CH_2Cl_2$ (125 ml) is added m-CPBA (8 g) with stirring, and stirring is continued for 15 h at 10° C. The temperature is raised to RT over a period of 2 h and the mixture is diluted with $CH_2Cl_2$ (400 ml). The mixture is transferred into a separatory funnel, and washed with cold saturated solution of $Na_2S_2O_3$ solution in water (2×400 ml). The organic layer is successively washed with cold saturated solution $NaHCO_3$ (400 ml) and cold brine (100 ml). The aqueous layers are extracted with $CH_2Cl_2$ (2×400 ml). The combined organic layers are dried ($Na_2SO_4$), filtered, and concentrated to dryness. The crude product is purified by column chromatography (silica) to give compound 10 (4 g).

Synthesis of Compound 11:

CuCN (1.5 g) is dried in high vacuum at 150° C. for 30 min, suspended in dry THF (25 ml) and cooled down to −78° C. MeLi (1.6 M in $Et_2O$, 22.5 ml) is added slowly via syringe and the temperature is raised to −10° C. over a period of 30 min. The mixture is again cooled down to −78° C., followed by the addition of $BF_3$ etherate (1.4 ml) in THF (5 ml). After stirring for 20 min, compound 10 (1 g) in THF (25 ml) is added and stirring is continued for 5 h at −78° C. The excess of MeLi is quenched with a mixture of MeOH (10 ml) and $Et_3N$ (10 ml). The mixture is diluted with $Et_2O$ (250 ml) and transferred into a reparatory funnel and extracted with aqueous 25% $NH_3$/satd. $NH_4Cl$ (1:9) solution. The organic layer is successively washed with brine (150 ml), 5% AcOH (150 ml), saturated solution of $NaHCO_3$ (150 ml), and brine (150 ml). The aqueous layers are extracted with $Et_2O$ (2×250 ml). The combined organic layers are dried ($Na_2SO_4$), filtered, and concentrated to dryness. The crude product is purified by column chromatography (silica) to give compound 11 (800 mg).

Synthesis of Compound 13:

A solution of $Br_2$ (0.08 ml) in $CH_2Cl_2$ (1 ml) is added dropwise at 0° C. to a solution of commercially available (Carbosynth Ltd., Compton, Berkshire, UK) compound 12 (640 mg) in $CH_2Cl_2$ (10 ml) and stirred at 0° C. for 1 h. Cyclohexene (0.02 ml) is added and the reaction mixture is stirred for anther 30 min. The mixture is added dropwise to a solution of 11 (310 mg) and $Et_4NBr$ (280 mg, oven dried at 200° C.) in DMF/$CH_2Cl_2$ (20 ml, 1:1) containing molecular sieve (1 g, 3 A) with stirring at RT. The stirring is continued for 60 h. The reaction is quenched with pyridine (2 ml), filtered over celite, and washed with $CH_2Cl_2$ (20 ml). The solution is washed with brine (50 ml) and the aqueous layer is extracted 3 times with $CH_2Cl_2$ (3×50 ml). The combined organic layers are dried ($Na_2SO_4$), filtered, and concentrated to dryness. The crude product is purified by column chromatography (silica) to give compound 13 (144 mg).

Synthesis of Compound 14:

To a solution of compound 13 (140 mg) in THF (5 ml), TBAF (0.39 ml) is added. After 24 h additional TBAF (0.2 ml) is added and the stirring is continued for 50 h. The reaction mixture is concentrated to dryness and the crude product is purified by column chromatography (silica) to afford compound 14 (95 mg).

Synthesis of Compound 16:

A mixture of compound 14 (0.16 g) and compound 15 (0.35 g, synthesized as described by Banteli et al., Helvetica Chimica Acta 83:2893-2907, 2000) is co-evaporated with toluene twice and then dried under vacuum. The mixture is dissolved in dry $CH_2Cl_2$ (10 ml) and stirred with flame dried molecular sieve (4 A) and 2,6-di-tert-Bu-pyridine (0.59 ml) for 30 min at RT. The reaction mixture is cooled to 0° C. and MeOTf (0.25 ml) is added with stirring. The reaction mixture is stirred for 4 h at RT, filtered through a bed of Celite, washed with $CH_2Cl_2$ (2×10 ml) and then transferred to a reparatory funnel. The organic layer is washed with a cold saturated solution of $NaHCO_3$ (25 ml) and brine (25 ml), dried ($Na_2SO_4$), filtered, and concentrated to dryness. The residue is purified by column chromatography (silica) to give compound 16 (0.23 g).

Synthesis of Compound 17:

Compound 16 (0.96 mg) is dissolved in dioxane-water (10:2, 12 ml) and AcOH (0.2 ml) is added. 10% Pd/C (0.8 g) is added and stirred vigorously under hydrogen (40 psi) for 16 h at RT. The reaction mixture is filtered through a bed of Celite and washed with MeOH. Solvent is evaporated off to give compound 17 (700 mg).

Synthesis of Compound 18:

Compound 17 (500 mg) is treated at RT with 0.01N NaOMe in MeOH (20 ml) for 1 h. The reaction is neutralized with AcOH and the solvent is evaporated off to give compound 18 (300 mg).

Synthesis of Compound 19:

Compound 18 (200 mg) is dissolved in ethylenediamine (3 ml) and the solution is stirred for 3 h at 70° C. Solvent is evaporated off and the residue is purified by Sep-Pak C18 column to give compound 19 (160 mg).

Synthesis of Compound 21:

Commercially available (Aldrich Chemical Co., Milwaukee, Wi.) compound 20 (1.47 g) is suspended in $CH_2Cl_2$ (70 ml). To this suspension is added a solution of $(BOC)_2O$ (3.86 g in 70 ml of $CH_2Cl_2$) dropwise with stirring at RT. The stirring is continued for 2 h. The reaction mixture is concentrated to dryness and purified by column chromatography (CombiFlash) to give compound 21 (1.8 g).

Synthesis of Compound 23:

A suspension of compound 21 (1.59 g), commercially available (Aldrich Chemical Co., Milwaukee, Wis.) compound 22 (0.8 g) and $K_2CO_3$ (0.48 g) in DMF (15 ml) is stirred at 60° C. overnight. The reaction mixture is concentrated to a thick oil and filtered through a glass syringe filter, dissolved in $CH_2Cl_2$ and purified by column chromatography (silica) to give compound 23 (1.96 g).

Synthesis of Compound 24:

To a cold (0° C.) solution of compound 23 (0.99 g) in THF (30 ml) is added $LiAlH_4$ (2M solution in THF, 3.05 ml) with stirring. Stirring is continued for 2 h at 0° C. The reaction is quenched with EtOAc and diethylether is added. The mixture is transferred to a reparatory funnel and washed with cold saturated solution of $NH_4Cl$. The organic layer is dried ($Na_2SO_4$), filtered, and concentrated to dryness. The residue is purified column chromatography (CombiFlash) to give compound 24 (717 mg).

Synthesis of Compound 25:

A solution of $(COCl)_2$ (0.15 ml) in $CH_2Cl_2$ (3 ml) is cooled down to −78° C. To this solution is added DMSO (0.25 ml) dropwise in the cold (−78° C.) with stirring and stirring is continued for 15 min at −78° C. Compound 24 (717 mg) in $CH_2Cl_2$ (3 ml) is added dropwise to the above mixture at −78° C. with stirring. The stirring is continued for 15 min at −78° C. and DIPEA (1.17 ml) is added and stirred for 15 min. The reaction mixture is warmed to RT slowly. The reaction mixture is concentrated to dryness and the crude product is purified by column chromatography (silica) to give compound 25 (701 mg).

Synthesis of Compound 26:

Compound 25 (77 mg) is dissolved in $CH_2Cl_2$ (7 ml) and $CF_3COOH$ (1.4 ml) is added with stirring. The reaction mixture is stirred at RT for 2 h, $CF_3COOH$ (0.7 ml) is added and stirring is continued for another 1 h. The reaction mixture is evaporated to dryness and purified by Sep-Pak C18 Cartridges to give compound 26 (30 mg).

Synthesis of Compound 27:

To a solution of compound 19 (5 mg) in DMSO (0.2 ml) is added compound 26 (4 mg) and $NaBH_3CN$ (0.8 mg, 0.08 ml from a stock solution of 10 mg/ml) and AcOH (0.8 mg, 0.08 ml from a stock solution of 10 mg/ml). The reaction mixture is stirred at 60° C. for 2 h and the solvent is evaporated off. The residue is purified by HPLC (reverse phase C18 column) to give compound 27 (2.5 mg) which is heterobifunctional Compound #1 (also referred to herein as "Compound #1").

Example 2

Figure 2A:
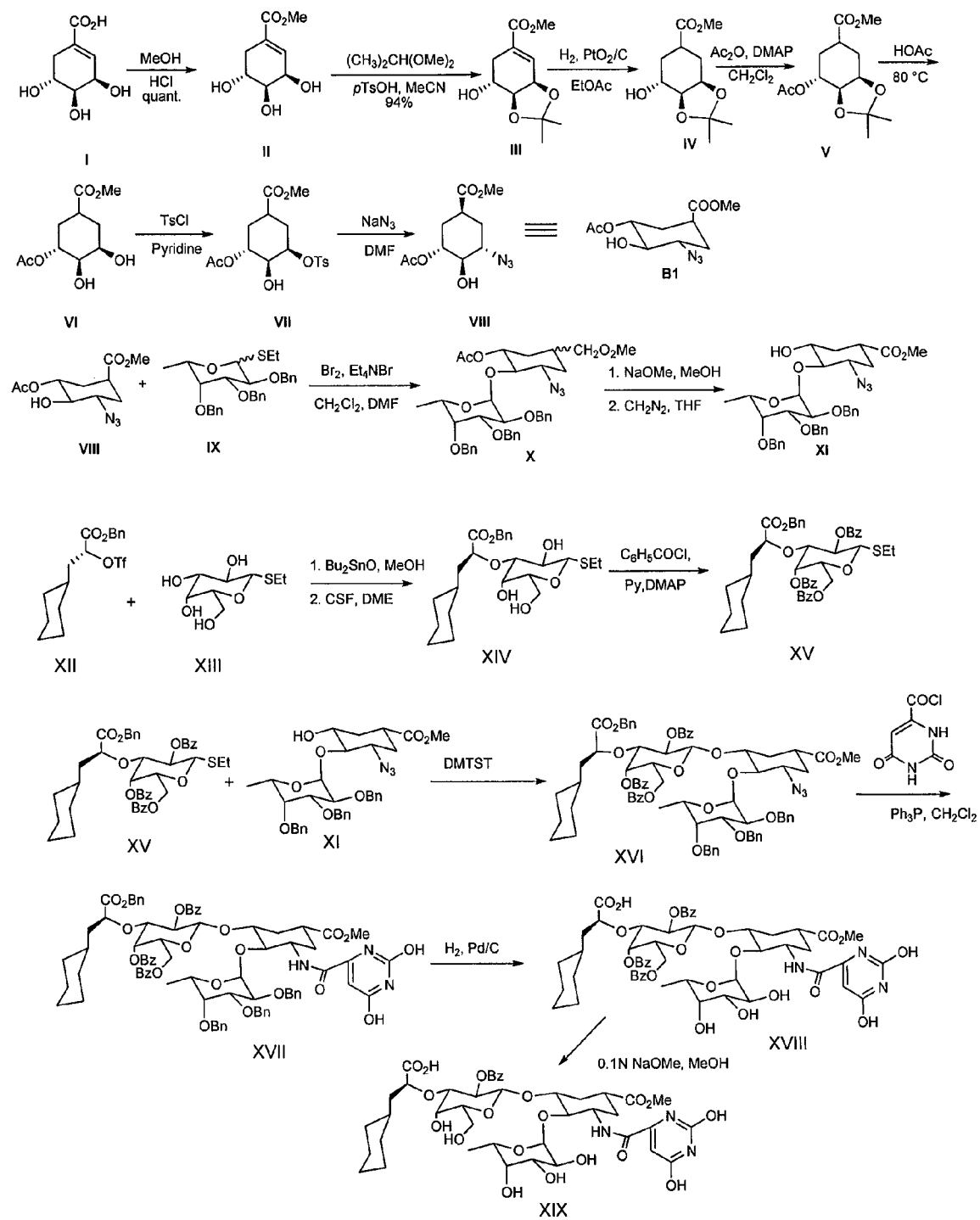
FIG. 2 (FIG. 2A, FIG. 2B and FIG. 2C) is a diagram illustrating the synthesis of heterobifunctional Compound #2 (compound 28).
Figure 2B:
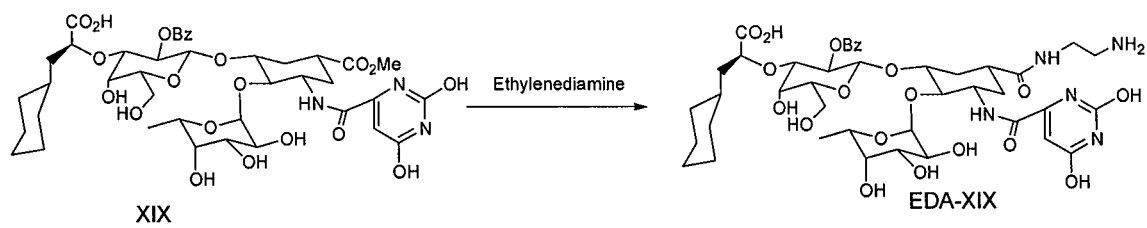
Figure 2C:
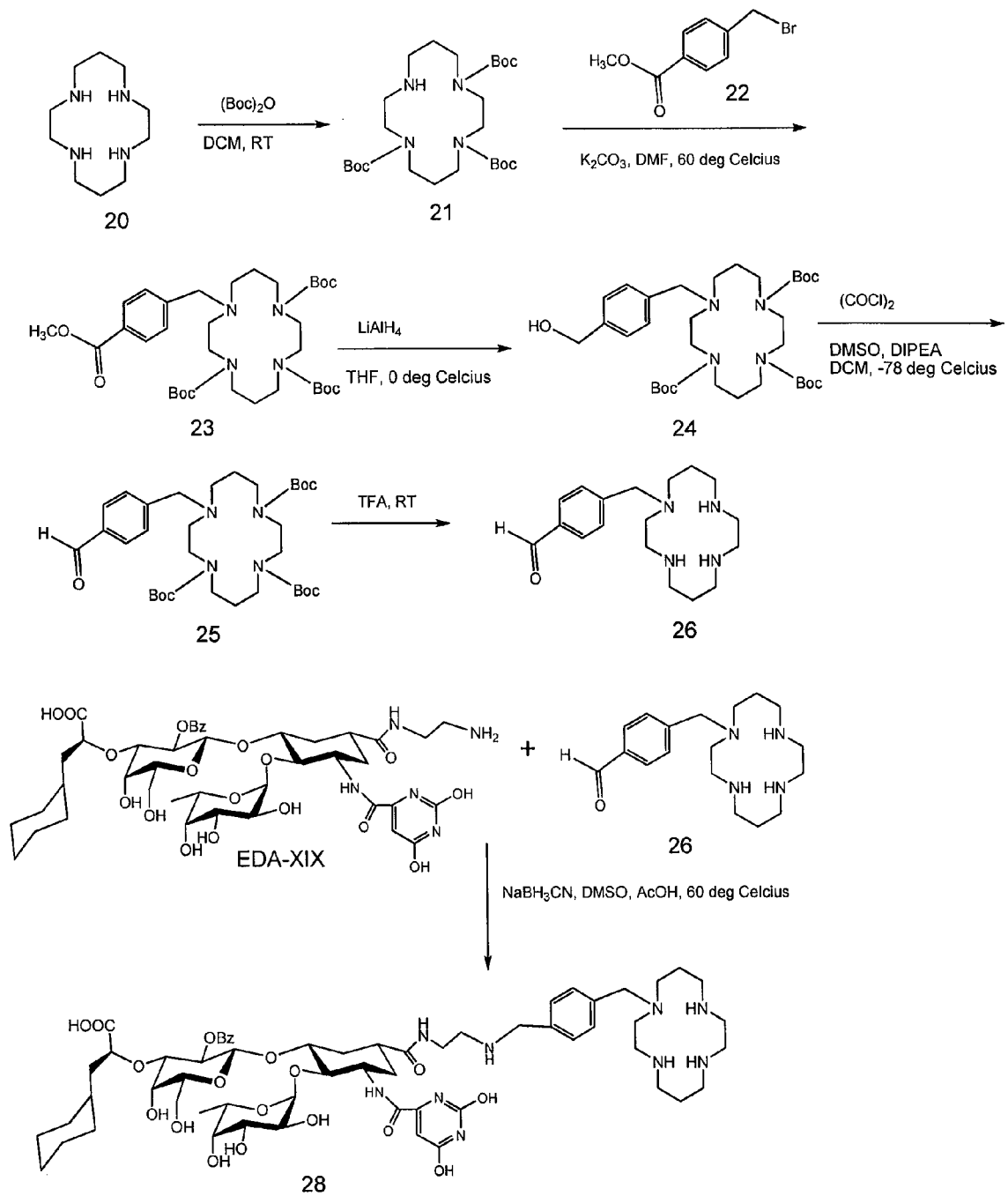

Synthesis of Heterobifunctional Compound #2 (Compound 28 of FIG. 2)

Synthesis of Intermediate II:

(−)-Shikimic acid (20 g) in MeOH (200 ml) and sulfuric acid (2 ml, 98%) are stirred at rt for 50 h. The reaction mixture is neutralized with 2N aqueous NaOH in the cold. After evaporation to dryness, the residue is purified by silica gel chromatography to afford II (19.2 g).

Synthesis of Intermediate (III):

Methyl shikimate (II, 10 g), 2,2 dimethoxypropane (10 ml) and p-TsOH (0.8 g) are dissolved in acetonitrile (125 ml) and stirred at rt for 1 h. The reaction mixture is then neutralized with triethylamine (2 ml) and evaporated to dryness. The residue is chromatographed on silica gel to yield III (11 g).

Synthesis of Intermediate IV:

The shikimic acid derivative III (10 g) and $PtO_2/C$ (10%, 250 mg) in MeOH (40 ml) are hydrogenated at rt under vigorous stirring. After 16 h the reaction mixture is filtered over celite and evaporated to dryness. The residue is chromatographed on silica gel to yield IV.

Synthesis of Intermediate V:

To a solution of IV (8 g) in DCM (100 ml) at 0° C. are added pyridine (12 ml), acetic anhydride (7 ml) and a DMAP (25 mg). The reaction mixture is stirred at rt for 1 h, and diluted with EtOAc (250 ml). After washing with 0.5 M aqueous HCl (3×50 ml), saturated solution of $KHCO_3$ (3×50 ml) and brine (3×50 ml), the combined organic layers are dried ($Na_2SO_4$) and evaporated to dryness. The residue is purified by chromatography on silica gel to yield V (6.8 g).

Synthesis of Intermediate VI:

A solution of V (6.0 g) in acetic acid (30 ml, 80%) is stirred at 80° C. for 1 h. Solvent is evaporated off and the residue is purified by chromatography on silica gel (DCM/MeOH 14:1) to yield VI (3.6 g).

Synthesis of Intermediate (VII):

A solution of VI (3 g) and p-TsCl (3.5 g) in pyridine (30 ml) is stirred at rt for 6 h. MeOH (5 ml) is added and the solvent is evaporated at reduced pressure, the residue dissolved in EtOAc (3×150 ml) and the organic layers are washed with 0.5 M aqueous HCl (0° C.), water (cold) and brine (cold). The combined organic layers are dried ($Na_2SO_4$), filtered on Celite and evaporated to dryness. The residue is purified by chromatography on silica gel (toluene/EtOAc 4:1) to yield VII (3.7 g).

Synthesis of Compound VIII:

A solution of VII (3 g) and $NaN_3$ (2.5 g) in DMF (20 ml) is stirred at 80° C. The reaction mixture is cooled to rt and diluted with EtOAc (200 ml) and water (50 ml). The organic layer is additionally washed twice with water (2×50 ml) and once with brine (50 ml). All aqueous layers are extracted twice with EtOAc (2×50 ml). The combined organic layers are dried with $Na_2SO_4$, filtered and the solvent is evaporated off. The residue is purified by chromatography on silica gel (petroleum ether/EtOAc 5:2) to give VIII (2.2 g).

Synthesis of Compound X:

To a solution of ethyl 2,3,4-tri-O-benzyl-α-L-fucothiopyanoside IX (1.5 g) in DCM (3 ml), bromine (150 μl) is added at 0° C. under argon. After 5 min the cooling bath is removed and the reaction mixture is stirred for additional 25 min at rt. Cyclohexene (200 μl) is added and the reaction mixture is added to a solution of VIII (400 mg), $(Et)_4NBr$ (750 mg) and powdered 4 Å molecular sieves in DCM (10 ml) and DMF (5 ml). After 16 h, triethylamine (1.5 ml) is added and stirred for an additional 10 min, diluted with EtOAc (50 ml) and washed with sat. aqueous $NaHCO_3$, water and brine. The aqueous layers are extracted twice with EtOAc (2×50 ml). The combined organic layers are dried ($Na_2SO_4$), filtered and evaporated to dryness. The residue is purified by chromatography on silica gel (toluene/EtOAc 9:1) to yield X (700 mg).

Synthesis of Compound XI:

To a solution of X (1.5 g) in MeOH (20 ml) is added freshly prepared NaOMe (80 mg) and the reaction mixture is stirred in a pressure tube at 80° C. for 20 h. The reaction mixture is cooled to rt and neutralized with acetic acid. Solvent is evaporated to dryness and the residue is dissolved in ether. Freshly prepared diazomethane is added and the excess diazomethane is neutralized with acetic acid. Solvent is evaporated off to give XI (1.25 g).

Synthesis of Building Block XV:

This synthesis is done exactly in same way as described previously (*Helvetica Chemica Acta* 83:2893-2907 (2000)).

Synthesis of Compound XVI:

A mixture of XI (1.6 g), XV (3 g) and activated powdered molecular sieves 4 Å (1 g) in DCM (17 ml) is stirred at rt under argon for 2 h. Then DMTST (2 g) is added in 4 equal portions over a period of 1.5 h. After 24 h the reaction mixture is filtered over Celite and the filtrate is diluted with DCM (100 ml). The organic layer is washed with sat. aqueous $NaHCO_3$ and brine and the aqueous layers are extracted twice with DCM. The combined organic layers are dried ($Na_2SO_4$), filtered and evaporated to dryness. The residue is purified by chromatography on silica gel (toluene/EtOAc 8:1) to yield XVI (1.5 g).

Synthesis of Compound XVII:

To a solution of XVI (500 mg) and orotic acid chloride (500 mg) in dichloromethane (10 ml) is added a solution of triphenylphosphine (500 mg in 5 ml dichloromethane) dropwise during 10 min. The reaction mixture is stirred at rt for 25 h and the solvent is evaporated off. The residue is purified (chromatography on silica gel DCM/MeOH 19:1) to give XVII (250 mg).

Synthesis of Compound XVIII:

To a solution of XVII (200 mg) in dioxane-water (5:1, 12 ml) is added 10% Pd—C (100 mg) and the reaction mixture is stirred vigorously under hydrogen (55 psi) for 24 h. Catalyst is filtered through a bed of celite and the solvent is evaporated off. Residue is purified by silica gel chromatography to give compound XVIII (150 mg).

Synthesis of XIX:

To a solution of compound XVIII (145 mg) in MeOH (5 ml) is added a solution of NaOMe in MeOH (25%, 0.025 ml) and the reaction mixture is stirred at rt for 4 h, neutralized with acetic acid and the solvent is evaporated off. Residue is dissolved in water and passed through a bed of Dowex 50wX-8 (Na-form) resin. Water wash is evaporated off to afford compound XIX (100 mg).

Synthesis of EDA-XIX:

XIX (80 mg) is heated at 70° C. with ethylenediamine (EDA) (1 ml) with stirring for 5 h. Solvent is evaporated off and the purified by sephadex G-25 column to give EDA-XIX (82 mg).

Synthesis of Compound 28:

Compound 26 of Example 1 is reacted with EDA-XIX (and the product purified) using the procedures described in Example 1 (for the synthesis of compound 27) to give compound 28 which is heterobifunctional Compound #2 (also referred to herein as "Compound #2").

Example 3

Assay to Assess Binding of Compounds to CXCR4

Methods

The assay assesses the ability of glycomimetic compounds to inhibit binding of an anti-CXCR4 antibody conjugated to phycoerythrin ("PE"), to CXCR4 on the surface of SupT1 cells. SupT1 cells are a T lymphoblast derived from a lymphoblastic leukemia and constitutively express CXCR4 on the cell surface. The cells are purchased from ATCC (ATCC number CRL-1942). Anti-human CXCR4-phycoerythrin monoclonal antibody (anti-CXCR4-PE) is purchased from R&D Systems (catalog number FAB170P, clone 12G5). The cells are grown in RPMI 1640 medium supplemented with 10% FBS. Approximately $2 \times 10^6$ cells are washed three times by centrifuging the cells at 400×g for 10 minutes and the cell pellet is resuspended in PBS plus 0.05% BSA. After the third centrifugation, the cell pellet is resuspended in PBS plus BSA to a concentration of $5 \times 10^5$ cells per ml. To block non-specific binding, human 1 g is added to the cells to a concentration of 1 μg per $10^5$ cells. Next, 200 μl ($1 \times 10^5$ cells) are added to 5 ml polypropylene round-bottom tubes (Falcon 2063 tubes). Compound #1 (Example 1) (lot 31-190) is added to the cells at final concentrations of 0.5, 5, 10, and 50 μM. To achieve a final concentration of 0.5 μM, 2.2 μl of 50 μM Compound #1 plus 19.8 μl of PBS/BSA are added to 200 μl of cells. To achieve a final concentration of 5 μM, 22 μl of 50 μM Compound #1 are added to 200 μl of cells. To achieve a final concentration of 10 μM, 4.4 μl of 500 μM Compound #1 plus 17.6 μl of PBS/BSA are added to 200 μl of cells. To achieve a final concentration of 50 μM, 22 μl of 500 μM Compound #1 are added to 200 μl of cells. Other aliquots of cells are treated with either 1 or 5 μM of the bicyclam CXCR4 antagonist AMD-3100 (Sigma Aldrich, catalog #A5602). To achieve a final concentration of 1 μM AMD-3100, 4.4 μl of 50 μM AMD-3100 plus 17.6 μl of PBS/BSA are added to 200 μl of cells and to achieve a final concentration of 5 μM, 22 μl of 50 μM AMD-3100 are added to 200 μl of cells. In addition, one tube of cells is treated with 1 μg/ml of SDF-1α (R&D Systems catalog #350-NS), the natural ligand of CXCR4. The tubes are placed at 4° C. for 15 minutes. Subsequently, each tube receives 10 μl of anti-CXCR4-PE, except one tube of cells receives 10 μl of mouse IgG 2A isotype control antibody. The tubes are incubated at 4° C. for 45 minutes. The cells are washed twice with PBS plus 0.05% BSA and the final cell pellet is resuspended in 100 μl of PBS/BSA. To fix the samples, 100 μl of 2% formaldehyde (Polysciences, Inc. ultrapure EM grade, catalog number 04018) are added to each tube. Flow cytometry is performed using a Cytomation MoFlo instrument.

Results

Figure 3:
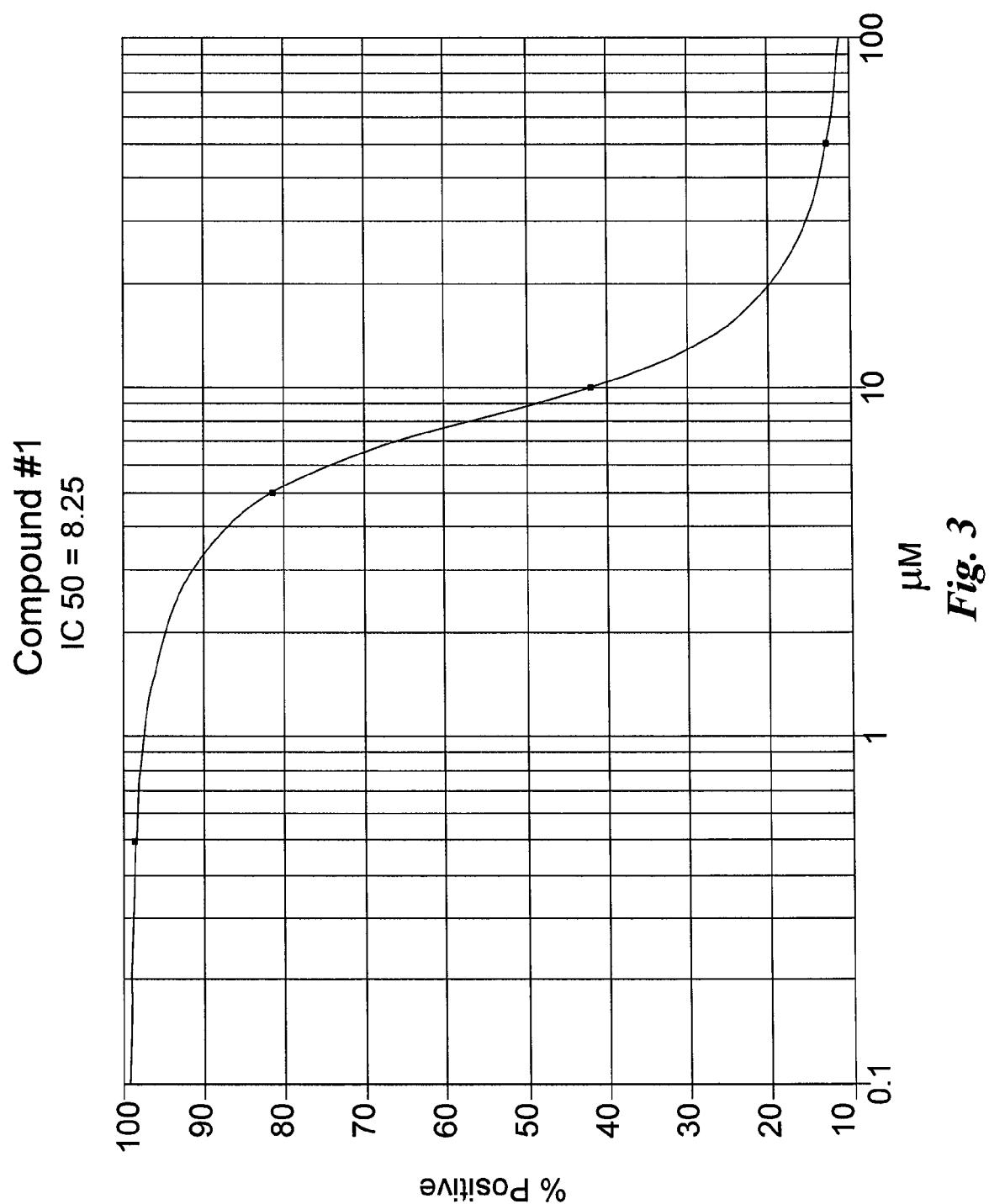
FIG. 3 depicts the inhibition of binding of anti-CXCR4-PE to SupT1 cells in a dose-dependent manner by heterobifunctional Compound #1.

As shown in the table below, Compound #1 inhibits binding of anti-CXCR4-PE to SupT1 cells in a dose-dependent manner with an $IC_{50}$ of 8.25 μM (FIG. 3). SDF-1α efficiently inhibits binding of the antibody to CXCR4.

|  | % positive | Mean fluorescence intensity | Median fluorescence intensity |
|---|---|---|---|
| SupT1 cells only | 1.13 | 2.80 | 2.55 |
| Isotype control | 1.46 | 4.73 | 2.46 |
| No inhibitor | 99.28 | 104.75 | 86.60 |
| 0.5 μM Compound #1 | 98.69 | 68.49 | 54.25 |
| 5 μM Compound #1 | 81.48 | 22.25 | 13.34 |
| 10 μM Compound #1 | 42.06 | 14.08 | 6.04 |
| 50 μM Compound #1 | 12.80 | 11.08 | 3.92 |
| 1 μM AMD-3100 | 57.57 | 15.60 | 7.77 |
| 5 μM AMD-3100 | 12.42 | 9.98 | 3.92 |
| 1 μg/ml SDF-1α | 12.37 | 10.25 | 4.07 |

Example 4

E-Selectin Activity

Binding Assay

Methods

The inhibition assay to screen glycomimetic antagonists of E-selectin is a competitive binding assay, which allows the determination of $IC_{50}$ values. Briefly, E-selectin/Ig chimera is immobilized by incubation at 37° C. in 96 well microtiter plates for 2 hours. To reduce nonspecific binding, bovine serum albumin is added to each well and incubated at room temperature for 2 hours. The plate is washed and serial dilutions of the test compounds are added to the wells in the presence of conjugates of biotinylated, $sLe^a$ polyacrylamide with streptavidin/horseradishperoxidase and incubated for 2 hours at room temperature. To determine the amount of $sLe^a$ bound to immobilized E-selectin after washing, the peroxidase substrate, 3,3',5,5' tetramethylbenzidin (TMB) is added. After 3 minutes, the enzyme reaction is stopped by the addition of $H_3PO_4$ and the absorbance of light at a wavelength of 450 nm is determined. The concentration of test compound required to inhibit binding by 50% is determined and reported as the $IC_{50}$ value for each glycomimetic E-selectin antagonist. In addition to reporting the absolute $IC_{50}$ value as measured above, relative $IC_{50}$ values are determined by a ratio of the $IC_{50}$ measured for the test compound to that of an internal control (reference) stated for each assay.

Results

Figure 4:
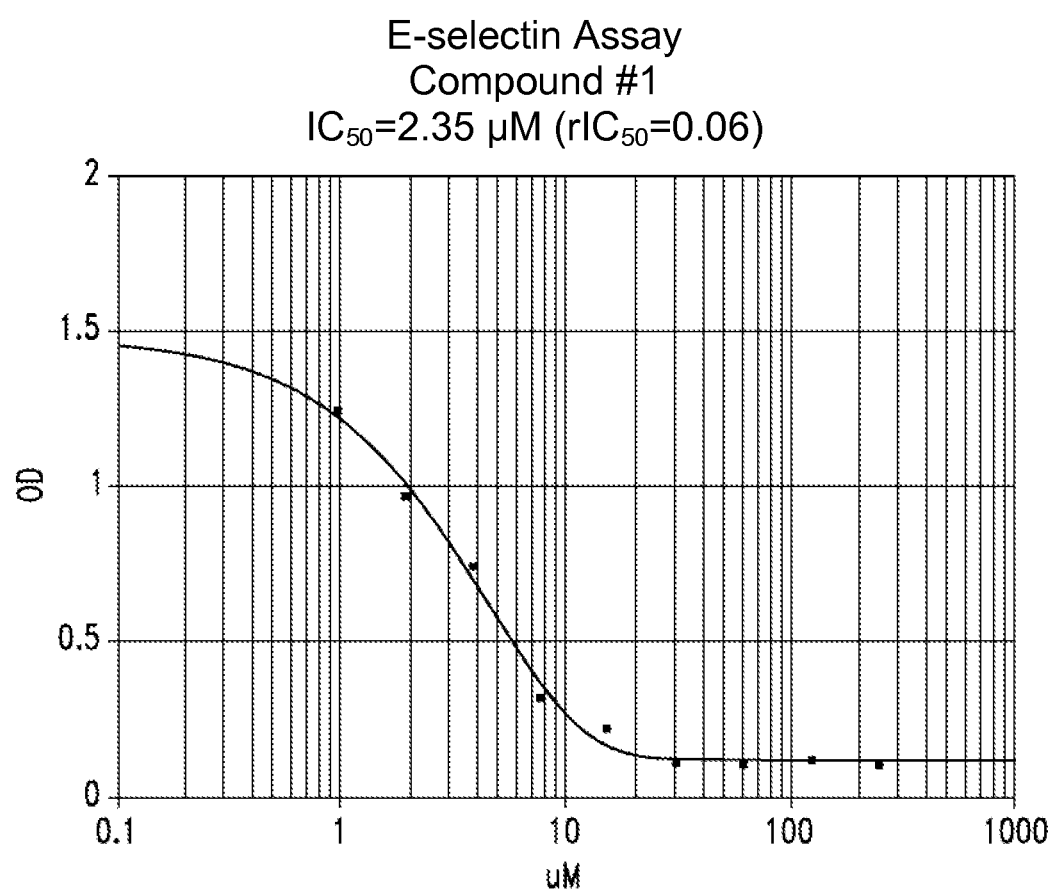
FIG. 4 depicts the results of an E-selectin assay in which heterobifunctional Compound #1 is used as the inhibitor.
Figure 5:
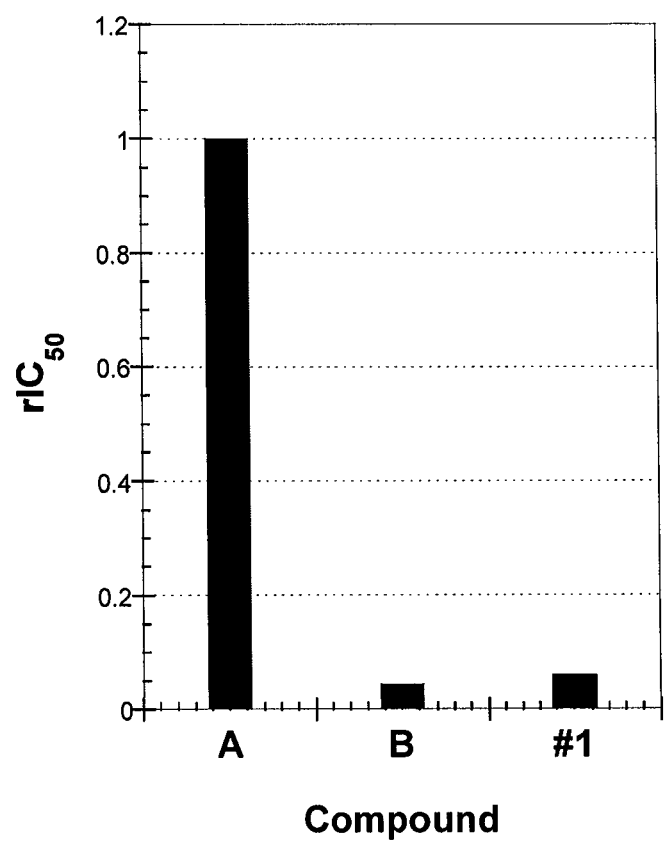
FIG. 5 depicts a comparison of IC$_{50}$ values of compounds A, B and #1 for E-selectin. Compound A, which is a known E-selectin inhibitor, is compound 15 of Thoma et al. (J. Med. Chem. 42:4909-4913, 1999) and is used as a reference compound. Compound #1 is heterobifunctional Compound #1. Compound B is the glycomimetic portion of Compound #1 (i.e., compound 18 of FIG. 1 except modified to replace COOMe, which is used in the linking process, with H).

The results for heterobifunctional Compound #1 are shown in FIGS. 4 and 5. Compound #1 is a potent E-selectin antagonist (as well as possessing anti-CXCR4 activity—FIG. 3).

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A heterobifunctional compound for inhibition of E-selectin and the CXCR4 chemokine receptor, comprising E-selectin inhibitor-Linker-CXCR4 chemokine receptor inhibitor, or a physiologically acceptable salt thereof, where the E-selectin inhibitor is not an antibody.

2. The compound of claim 1 wherein the E-selectin inhibitor is a small organic molecule.

3. The compound of claim 1 wherein the E-selectin inhibitor consists of:

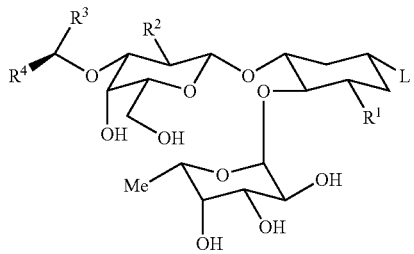

wherein:
L=end of bond to Linker;
R¹=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)OX, alkanyl substituted with C(=O)OX, C(=O)NHX, alkanyl substituted with C(=O)NHX, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)X, OX, NHX, NHC(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH;
R²=—OH,

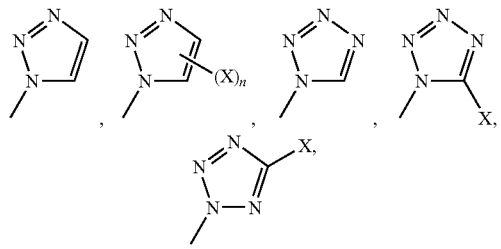

—O—C(=O)—X, —NH₂, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

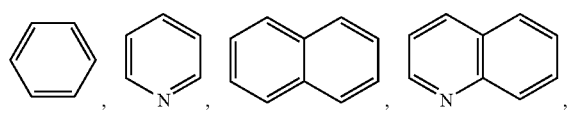

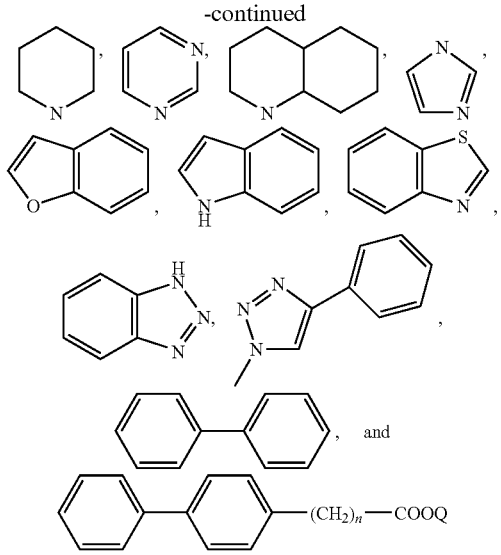

where Q is H or a physiologically acceptable salt, $C_1$-$C_8$ alkanyl, $C_1$-$C_8$ alkenyl, $C_1$-$C_8$ alkynyl, aryl, $(CH_2)_m$-aryl where m is 1-10, and where n=0-10, and any of the above ring compounds may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl, $C_1$-$C_{14}$ aryl, or OY, C(=O)OY, $NY_2$ or C(=O)NHY where Y is H, $C_1$-$C_8$ alkanyl, $C_1$-$C_8$ alkenyl, $C_1$-$C_8$ alkynyl, or $C_1$-$C_{14}$ aryl;
R³=H, $C_1$-$C_8$ alkanyl, $C_1$-$C_8$ alkenyl, $C_1$-$C_8$ alkynyl, CN, $CH_2CN$, C(=O)X where X is H, $C_1$-$C_8$ alkanyl, $C_1$-$C_8$ alkenyl, $C_1$-$C_8$ alkynyl, NHOH, $NHOCH_3$, NHCN, or $NX_2$, or C(=O)OY where Y is H, C alkanyl, C alkenyl or $C_1$-$C_8$ alkynyl; and

R⁴ = where the cyclopropane ring may be substituted with one to two, and the cyclohexane ring may be substituted with one to three, independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl.

4. The compound of claim 3 wherein the E-selectin inhibitor consists of:

wherein L=end of bond to Linker.

5. The compound of claim 3 wherein the E-selectin inhibitor consists of:

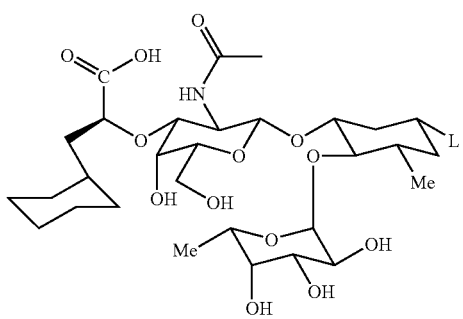

wherein L=end of bond to Linker.

6. The compound of claim 3 wherein the E-selectin inhibitor consists of:

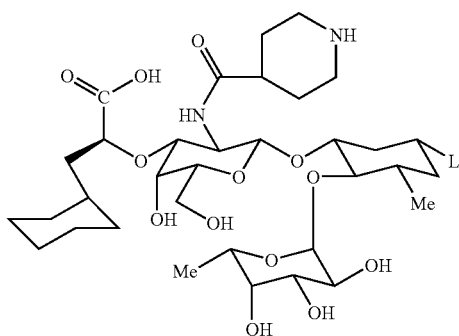

wherein L=end of bond to Linker.

7. The compound of claim 3 wherein the E-selectin inhibitor consists of:

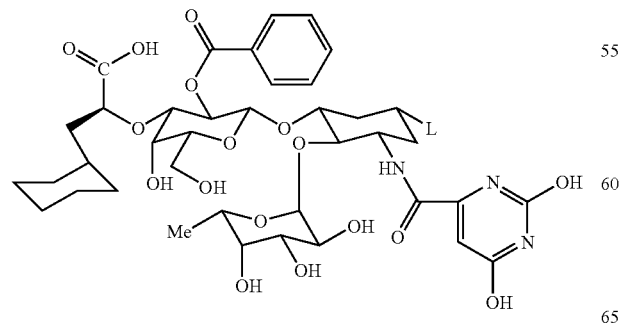

wherein L=end of bond to Linker.

8. The compound of claim 1 or claim 2 wherein the CXCR4 chemokine receptor inhibitor consists of:

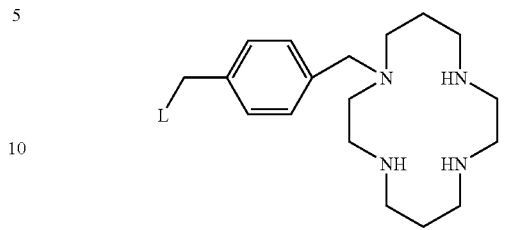

wherein L=end of bond to Linker.

9. The compound of claim 1 having the formula:

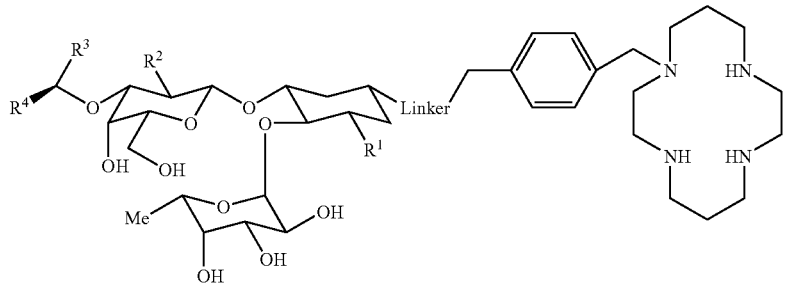

wherein:

$R^1$=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, OH, or NHX where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)OX, alkanyl substituted with C(=O)OX, C(=O)NHX, alkanyl substituted with C(=O)NHX, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH; C(=O)X, OX, NHX, NHC(=O)X, where X=H, $C_1$-$C_8$ alkanyl, $C_1$-$C_8$ alkenyl, $C_1$-$C_8$ alkynyl, halogenated $C_1$-$C_8$ alkanyl, aryl which may be substituted with one or more of Me, OMe, halide, or OH;

$R^2$=—OH,

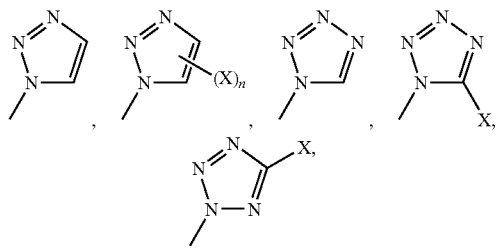

—O—C(=O)—X, —NH$_2$, —NH—C(=O)—NHX, or —NH—C(=O)—X where n=0-2 and X is independently selected from $C_1$-$C_8$ alkanyl, $C_1$-$C_8$ alkenyl, $C_1$-$C_8$ alkynyl,

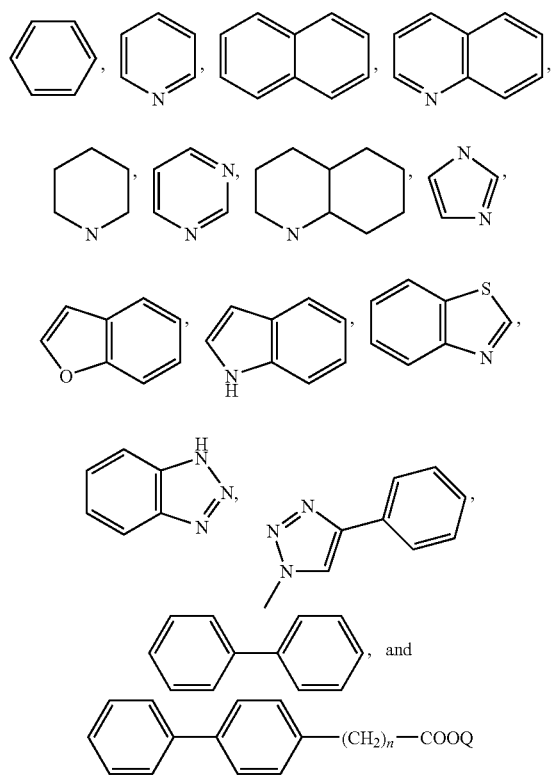

where Q is H or a physiologically acceptable salt, $C_1$-$C_8$ alkanyl, $C_1$-$C_8$ alkenyl, $C_1$-$C_8$ alkynyl, aryl, $(CH_2)_m$-aryl where m is 1-10, and where n=0-10, and any of the above ring compounds may be substituted with one to three independently selected of Cl, F, $CF_3$, $C_1$-$C_8$ alkoxy, $NO_2$, $C_1$-$C_8$ alkanyl, $C_1$-$C_8$ alkenyl, $C_1$-$C_8$ alkynyl, $C_1$-$C_{14}$ aryl, or OY, C(=O)OY, $NY_2$ or C(=O)NHY where Y is H, $C_1$-$C_8$ alkanyl, $C_1$-$C_8$ alkenyl, $C_1$-$C_8$ alkynyl, or $C_1$-$C_{14}$ aryl;

$R^3$=H, $C_1$-$C_8$ alkanyl, $C_1$-$C_8$ alkenyl, $C_1$-$C_8$ alkynyl, CN, $CH_2CN$, C(=O)X where X is H, $C_1$-$C_8$ alkanyl, $C_1$-$C_8$ alkenyl, $C_1$-$C_8$ alkynyl, NHOH, $NHOCH_3$, NHCN, or $NX_2$, or C(=O)OY where Y is H, $C_1$-$C_8$ alkanyl, $C_1$-$C_8$ alkenyl or $C_1$-$C_8$ alkynyl; and $R^4$ = ⌬, or ⬡ where the cyclopropane ring may be substituted with one to two, and the cyclohexane ring may be substituted with one to three, independently selected of Cl, F, $C_1$-$C_8$ alkanyl, $C_1$-$C_8$ alkenyl, $C_1$-$C_8$ alkynyl or OY where Y is H, $C_1$-$C_8$ alkanyl, $C_1$-$C_8$ alkenyl, $C_1$-$C_8$ alkynyl or $C_1$-$C_{14}$ aryl.

10. The compound of claim 1 having the formula:

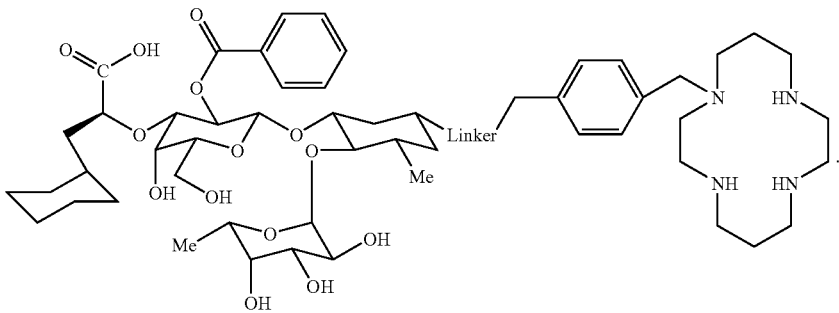

11. The compound of claim 1 having the formula:

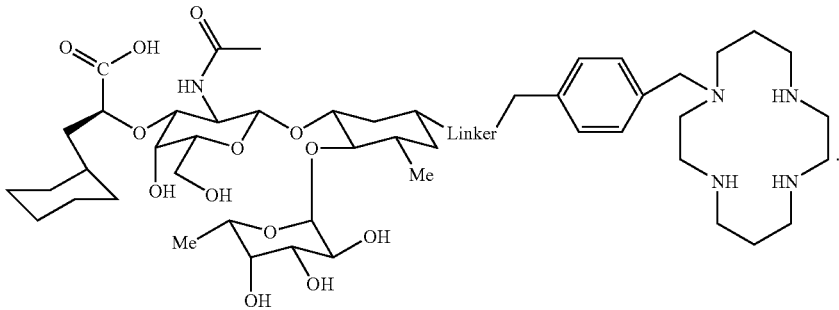

12. The compound of claim 1 having the formula:

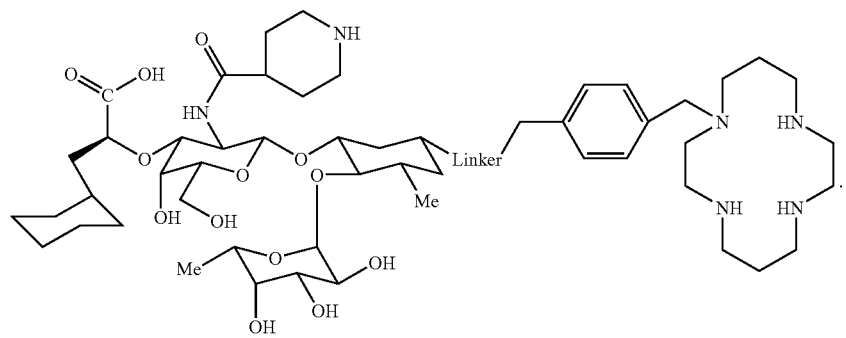

13. The compound of claim 1 having the formula:

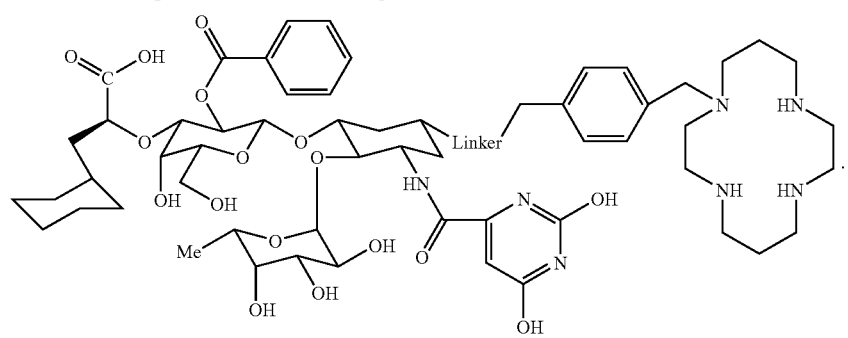

14. The compound of any one of claims 1-7, or 9-13, where Linker is one of:
(a) —C(=O)—NH—(CH₂)₂—NH—;
(b) —CH₂—NH—CH₂—; and
(c) —C(=O)—NH—CH₂—.

15. A method for inhibiting metastasis of a cancer in an individual who is in need thereof, comprising administering to the individual a compound in an amount effective for inhibiting metastasis, wherein the compound is according to claim 1 or claim 2 with or without a pharmaceutically acceptable carrier or diluent.

16. A method for inhibiting metastasis of a cancer in an individual who is in need thereof, comprising administering to the individual a compound in an amount effective for inhibiting metastasis wherein the compound is according to any one of claim 3, 9, 10 or 13 with or without a pharmaceutically acceptable carrier or diluent.

17. A method for mobilizing cancer cells from a site into the bloodstream and retaining the cancer cells in the bloodstream in an individual who is in need thereof, comprising administering to the individual a compound in an amount effective for said mobilizing and said retaining of the cancer cells, wherein the compound is according to claim 1 or claim 2 with or without a pharmaceutically acceptable carrier or diluent.

18. A method for mobilizing cancer cells from into the bloodstream and retaining the cancer cells in the bloodstream in an individual who is in need thereof, comprising administering to the individual a compound in an amount effective for said mobilizing and said retaining of the cancer cells, wherein the compound is according to any one of claim 3, 9, 10 or 13 with or without a pharmaceutically acceptable carrier or diluent.

19. A method for releasing cells into circulating blood and enhancing retention of the cells in the blood of an individual who is need of such treatment, comprising administering to the individual a compound in an amount effective for treatment, wherein the compound is according to claim 1 or claim 2 with or without a pharmaceutically acceptable carrier or diluent.

20. The method of claim 19, further including the step of collecting the cells released.

21. The method of claim 20 wherein the step of collecting utilizes apheresis.

22. The method of claim 19 wherein the cells are bone marrow progenitor cells.

23. A method for releasing cells into circulating blood and enhancing retention of the cells in the blood of an individual who is in need of such treatment, comprising administering to the individual a compound in an amount effective for treatment, wherein the compound is according to any one of claim 3, 9, 10 or 13 with or without a pharmaceutically acceptable carrier or diluent.

24. A method for the treatment of an inflammatory disease in which the adhesion or migration of cells occurs in the disease in an individual who is in need of such treatment, comprising administering to the individual a compound in an amount effective for treatment, wherein the compound is according to claim 1 or claim 2 with or without a pharmaceutically acceptable carrier or diluent.

25. A method for the treatment of an inflammatory disease in which the adhesion or migration of cells occurs in the disease in an individual who is in need of such treatment, comprising administering to the individual a compound in an amount effective for treatment, wherein the compound is according to any one of claim 3, 9, 10 or 13 with or without a pharmaceutically acceptable carrier or diluent.

26. The compound of any one of claims 1-7, and 9-13 in combination with a pharmaceutically acceptable carrier or diluent.

27. The compound of claim 9 or claim 10 having the formula:

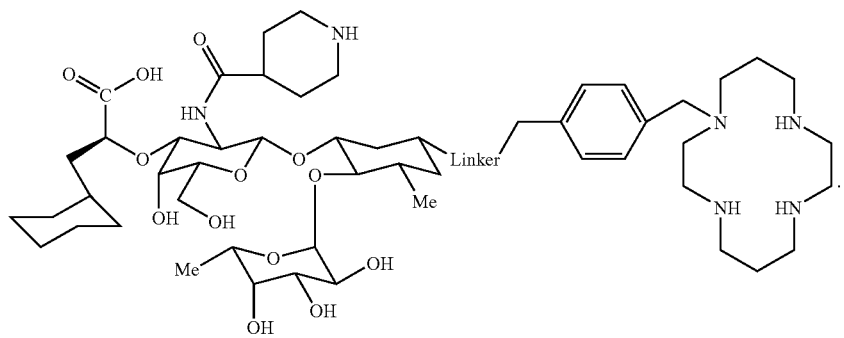

where Me is methyl.

28. The compound of claim 9 or claim 13 having the formula:

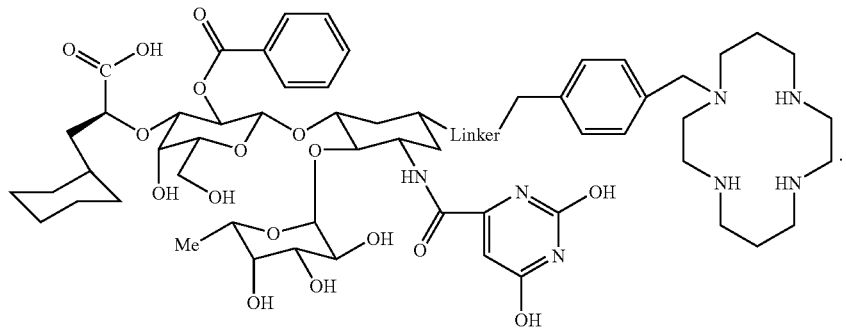

where Me is methyl.

29. The method of claim 23 wherein the cells are bone marrow progenitor cells.

30. The method of claim 23 further including the step of collecting the cells released.

31. The method of claim 30 wherein the step of collecting utilizes apheresis.

32. The compound of claim 8 where Linker is one of:
(a) —C(=O)—NH—(CH$_2$)$_2$—NH—;
(b) —CH$_2$—NH—CH$_2$—; and
(c) —C(=O)—NH—CH$_2$—.

33. The compound of claim 8 in combination with a pharmaceutically acceptable carrier or diluent.

* * * * *

UNITED STATES PATENT AND TRADEMARK OFFICE
CERTIFICATE OF CORRECTION

PATENT NO. : 8,410,066 B2  
APPLICATION NO. : 12/768173  
DATED : April 2, 2013  
INVENTOR(S) : John L. Magnani et al.

Page 1 of 1

It is certified that error appears in the above-identified patent and that said Letters Patent is hereby corrected as shown below:

Title Page 3, Column 1, lines 31 - 34,

<u>Item (56):</u>
"Datta and Takayama, "Isolation and purification of trehalose 6-mono- and 6,6'-dicorynomycolates from *Cornyebacterium matruchotii.* Structural characterization of 1H NMR," Carbohydrate Research 245: 151-158, 1993." should read, --Datta and Takayama, "Isolation and purification of trehalose 6-mono- and 6,6'-di-corynomycolates from *Corynebacterium matruchotii.* Structural characterization of 1H NMR," Carbohydrate Research 245: 151-158, 1993.--.

In the Claims

<u>Column 32, Line 34:</u>
"$NX_2$, or C(=O)OY where Y is H, C alkanyl, C alkenyl" should read, --$NX_2$, or C(=O)OY where Y is H, $C_1$-$C_8$ alkanyl, $C_1$-$C_8$ alkenyl--.

<u>Column 37, Line 46:</u>
"inhibiting metastasis wherein the compound is according to" should read, --inhibiting metastasis, wherein the compound is according to--.

<u>Column 37, Line 57:</u>
"18. A method for mobilizing cancer cells from into the" should read, --18. A method for mobilizing cancer cells from a site into the--.

Signed and Sealed this  
Sixteenth Day of July, 2013

Teresa Stanek Rea  
*Acting Director of the United States Patent and Trademark Office*